United States Patent [19]
Lenzen et al.

[11] Patent Number: 5,656,440
[45] Date of Patent: Aug. 12, 1997

[54] NUCLEOTIDE SEQUENCES CODING FOR THE BOVINE $\beta_3$-ADRENERGIC RECEPTOR (AR$\beta_3$) AND THEIR APPLICATIONS

[75] Inventors: Gerlinda Lenzen, Paris, France; Archana Kapoor, San Diego, Calif.

[73] Assignees: Virbac, Carros; Vetigen, Paris, both of France

[21] Appl. No.: 351,473

[22] PCT Filed: Apr. 21, 1994

[86] PCT No.: PCT/FR94/00447

§ 371 Date: Feb. 21, 1995

§ 102(e) Date: Feb. 21, 1995

[87] PCT Pub. No.: WO94/24162

PCT Pub. Date: Oct. 27, 1994

[30] Foreign Application Priority Data

Apr. 21, 1993 [FR] France ................... 93 04670

[51] Int. Cl.[6] .............. C12Q 1/00; C12N 15/09; C07K 14/705

[52] U.S. Cl. ............ 435/7.2; 536/23.5; 536/24.31; 435/69.1; 435/252.3; 435/254.11; 435/320.1; 435/325; 435/361; 530/350

[58] Field of Search .................... 530/350, 300; 435/7.2, 7.21, 69.1, 240.1, 252.3, 254.11, 320.1, 240.2; 536/23.1, 24.31, 23.5

[56] References Cited

PUBLICATIONS

Emorine et al., Science, vol. 245, pp. 1118–1121, 1989.
Nahmias et al., Embo Journal, vol. 10, pp. 3721–3727, 1991.
Casteilla et al., Biochemical J., vol. 297, Part 1, pp. 93–97, 1994.
Sambrook et al., Molecular Cloning, vol. 3, pp. 16.2–16.30 and 17.2–17.28, 1989, Cold Spring Harbor Lab. Press.
Benovic et al., Science, vol. 246, pp. 235–240, 1989.

*Primary Examiner*—Stephen Walsh
*Assistant Examiner*—Sally P. Teng
*Attorney, Agent, or Firm*—Oblon, Spivak, McClelland, Maier & Neustadt, P.C.

[57] ABSTRACT

Nucleotidic sequences coding for the bovine adrenergic-$\beta_3$ receiver (RA$\beta_3$), utilization of said sequences as probes and for the expression of peptides and/or fragments thereof having an activity of bovine RA$\beta_3$, vectors useful for said expression, as well as cellular hosts containing said vector. Polyclonal and monoclonal antibodies raised against said peptides and usable, particularly for the detection of bovine adrenergic-$\beta_3$ receivers, as well as method for screening substances, with agonist or antagonist action in relation to peptides having an adrenergic-$\beta_3$ receiver activity and kits for the detection of the affinity degrees of different substances for said peptides having an adrenergic-$\beta_3$ receiver activity. Transgenic and recombinant mice containing said nucleotidic sequence.

13 Claims, 10 Drawing Sheets

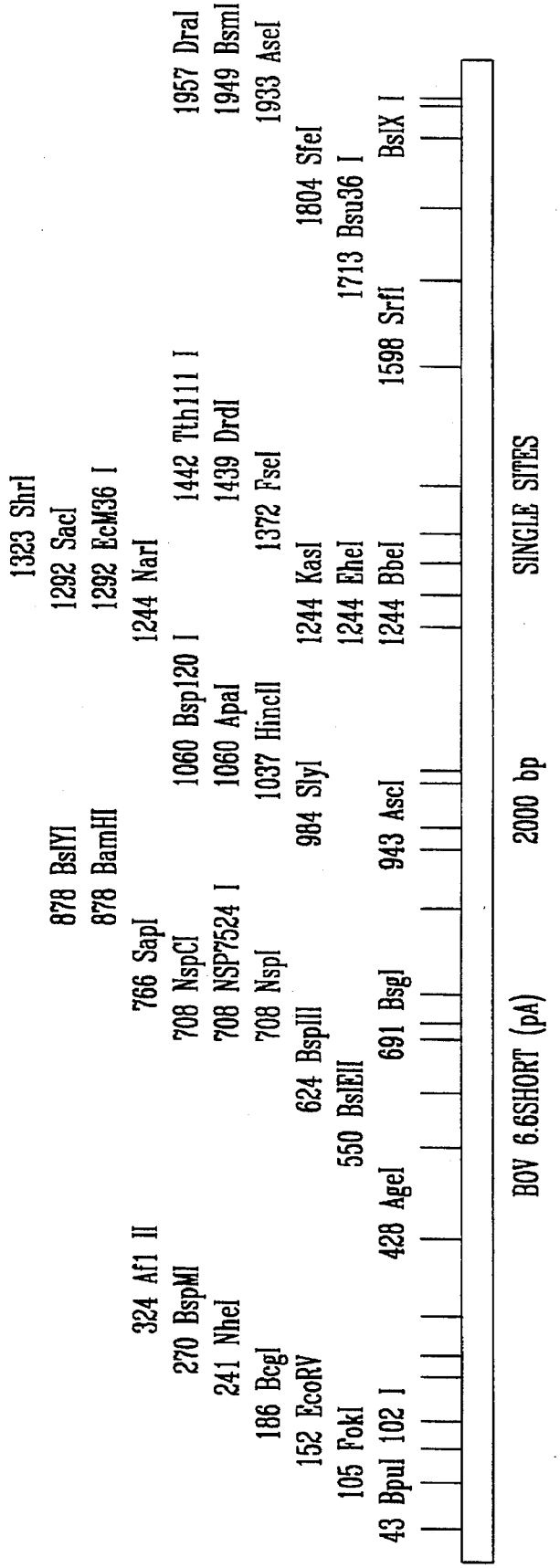
FIG. 1α

FIG. 2A

| | TM1 |
|---|---|
| BETA3 BOV | MAPWPPGNSSLTPWPDIPTLAPNTANASGLPGVPWAVA[LAGALLALAVLATVGGNLLLVIV] |
| BETA3 HU | MAPWPHENSSLAPWPDLPTLAPNTANTSGLPGVPWEA[ALAGALLALAVLATVGGNLLLVIV] |
| BETA3 RA | MAPWPHKNGSLAFWSDAPTLDPSAANTSGLPGVPWAAA[LAGALLALA---TVGGNLLVIT] |
| BETA3 MO | MAPWPHRNGSLALWSDAPTLDPSAANTSGLPGVPWAAA[LAGALLALA---TVGGNLLVII] |
| | ****  *.** *.. ** .*** *** .********* ***********  **********|

| | TM2 | TM3 |
|---|---|---|
| BETA3 BOV | AIARTPRLQTMTNVF[VTSLATADLVVGLLVVPPGATLAL]TGHWPLGVTG[CELWTSVDVLC] |
| BETA3 HU | AIAWTPRLQTMTNVF[VTSLAAADLVMGLLVMPPGATLAL]TGHWPLGATG[CELWTSVDVLC] |
| BETA3 RA | AIARTPRLQTITNVF[VTSLATADLVVGLLVMPPGATLAL]TGHWPLGATG[CELWTSVDVLC] |
| BETA3 MO | AIARTPRLQTITNVF[VTSLAAADLVVGLLVMPPGATLAL]TGHWPLGETG[CELWTSVDVLC] |
| | *** ********* ******* *********  ** .** **********|

| | TM4 |
|---|---|
| BETA3 BOV | VTASIETLCALAVDRYLAVTNPLRYGALVTKRRAL[AAVVLVWVSAAVSFAPIMSKWWRI] |
| BETA3 HU | VTASIETLCALAVDRYLAVTNPLRYGALVTKRCAR[TAVVLVWVSAAVSFAPIMSQWWRV] |
| BETA3 RA | VTASIETLCALAVDRYLAVTNPLRYGTLVTKRRAR[AAVVLVWISATVSFAPIVSAVSFAPIMSQWWRV] |
| BETA3 MO | VTASIETLCALAVDRYLAVTNPLRYGTLVTKRRAR[AAVVLVWISAAVSFAPIMSQWWRV] |
| | *********************** *****  * ********** *********** *** |

| | TM5 |
|---|---|
| BETA3 BOV | GADAEAQRCHSNPRCCCTFASNMPYALLSSSSVSFYLPLLVMLFVYARVFVVATRQLRLLRR |
| BETA3 HU | GADAEAQRCHSNPRCCAFASNMPYVLLSSSSVSFYLPLLVMLFVYARVFVVATRQLRLRG |
| BETA3 RA | GADAEAQECHSNPRCCSFASNMPYALLSSSSVSFYLPLLVMLFVYARVFVVAKRQRRLLRR |
| BETA3 MO | GADAEAQECHSNPRCCSFASNMPYALLSSSSVSFYLPLLVMLFVYARVFVVAKRQRHLLRR |
| | ******** ******* * ****** ****************** *****  * *** |

```
                                                                    TM6
BETA3 BOV    ELGRFPPEESPPAPSRSGSPGLAGPCASPAGVPSYGRRPARLLPLREHRALRTLGLIMGT
BETA3 HU     ELGRFPPEESPPAPSRSLAPAPVGTCAPPEGVPACGRRPARLLPLREHRALCTLGLIMGT
BETA3 RA     ELGRFPPEESPRSPSPSRSPSPATVGTPTASDGVPSCGRRPARLLPLGEHRALRTLGLIMGI
BETA3 MO     ELGRFSPEESPPSPSPSRSPSPATGGTPAAPDGVPPCGRRPARLLPLREHRALRTLGLIMGI
             ****.****.  .***  .*    ...  **  .*********** ********.*****

TM7
BETA3 BOV    FTLCWLPFFVVNVVRALGGPSLVSGPTFLALNWLGYANSAFNPLIYCRSPDFRSAFRRLL
BETA3 HU     FTLCWLPFFLANVLRALGGPSLVPGPAFLALNWLGYANSAFNPLIYCRSPDFRSAFRRLL
BETA3 RA     FSLCWLPFFLANVLRALVGPSLVPSGVFIALNWLGYANSAFNPLIYCRSPDFRDAFRRLL
BETA3 MO     FSLCWLPFFLANVLRALAGPSLVPSGVFIALNWLGYANSAFNPVIYCRSPDFRDAFRRLL
             *.*******. **.***  *** .*  *.************** *********.*****

BETA3 BOV    CRCR---PEEHLAAASPPRAPSGAPTALTSPAGPMQPPELDGASCGLS
BETA3 HU     CRCGRRLPEPCAAARPALFSGVPAARSSPAQPRLCQRLDGASWGVS
BETA3 RA     CSYGGRGPEEP---RVVTFPASPVASRQNSPLNRF-DGYEGERPFPT
BETA3 MO     CSYGGRGPEEP---RAVTFPASPVEARQSPPLNRF-DGYEGARPFPT
             * *      *                .        **      *
```

*FIG. 2B*

```
SPLICED HuB3 DNA ──▶  ATGGCTCCGTGGCCTCACGAGAACAGCTCTCTTGCCCATGGCCGGACCTCCCCACCCTGGCCGCCCAATACCGCCAACAC
                     *************** * ************ **** ***** ** ************ ****** ******
BOV B3 DNA:     ──▶  ATGGCTCCGTGGCCTCCTGGAACAGCTCTCTGACCCCTGTGGCCAGATATCCCCACCCTGGCACCCAATACTGCCAACGC
OPEN READING FRAME    10        20        30        40        50        60        70        80

CAGTGGGCTGCCAGGGGTTCCGTGGAGGCGGCCCTAGCCGGGCCCTGCTGGCGTCGGCGTGCTGGCCACCGTGGGGAG
                    ************* **** *** ** **** *** ** ***** *** ***** ******** ************
                    GAGTGGGCTGCCAGGGGTGCCCTGGGCGTGCCCTGGGGGCGCTGTTGGCGCTAGCGGTGCTGGCCACCGTGGGGAG
                     90       100       110       120       130       140       150       160

GCAACCTGCTGGTCATCGTGGCCATCGCTGCCTGACTCCGAGACTCCAGACCATGACCAAGCGTGTTCGTGACTTCGCTGGCC
                    ************ **** ********* **** ************************** ***************
                    GCAACCTGCTGGTAATCGTGGCCATCGCTGCCTGACCCCGAGACTCCAGACCATGACCAAGCGTGTTCGTGACTTCGCTGGCC
                    170       180       190       200       210       220       230       240

GCAGCCGACCTGGTGATGGACTCCTGGTTGTCCGTGGTGGTGGCCGGCCACCTTGGCGTGACTGGCCACTGGCCGTTGGGCGC
                    ************ **** ********* **** **** ***** ****** *** ************ ********
                    ACAGCCGACCTGGTTGGTGTGGGCTCCTGGTTGTCGTGCCCCGGGGGCCACGTTGGCGTTGGCGCCCACTGGCCGCCCTGGGCGT
                    250       260       270       280       290       300       310       320
```

FIG. 3A

```
           330       340       350       360       370       380       390       400
           -|-       -|-       -|-       -|-       -|-       -|-       -|-       -|-
      CACTGGCTGGCGAGCTGTGGACCTCGGTGTGGACGTGCTGTGTGTGACCGGCCAGCATCGAAACCCTGTGCCCTGGCCGTGG
      *** ** **************** **** *************************************************** ****
      CACCGGTTGCGAGCTGTGGACCTCAGTGGAGCTGCTGTGTGTGACCGGCCAGCATCGAAACCCTGTGCCCTGGGGTGG
           -|-       -|-       -|-       -|-       -|-       -|-       -|-       -|-
           330       340       350       360       370       380       390       400

410       420       430       440       450       460       470       480
           -|-       -|-       -|-       -|-       -|-       -|-       -|-       -|-
      ACCGCTACCTGGCTGTGACCAACCCGCTGCCTTACGGGACACTGGTCACCAAGGCGTGCGCCGGAGACAGCTGTGGTCCTG
      ********** ***** ******************** ******* *** ****** **** ******** ********
      ACCGCTACCTGGCCGTGACCAACCCGCTGCCTGCCTACGGCGCGCTGGTCACCAAGAACGCGCCCTAGCAGCCGTGGTCCTG
           -|-       -|-       -|-       -|-       -|-       -|-       -|-       -|-
           410       420       430       440       450       460       470       480

490       500       510       520       530       540       550       560
           -|-       -|-       -|-       -|-       -|-       -|-       -|-       -|-
      GTGTGGGTCGTGTCGGCCGCGGTGTCGTTTGCGCCCATCATGAGCCAGTGGTGGCGGTAGGGGCCGACGCCGAGGCGCA
      ******** ***** ************** ************************* * ****************************
      GTGTGGGTGGTGTCGGCCGCGGTGTCGTTTGCGCCCATCATGAGCAAATGGTGGCGGCATCGGGGCCGATGCCGAGGCGCA
           -|-       -|-       -|-       -|-       -|-       -|-       -|-       -|-
           490       500       510       520       530       540       550       560

570       580       590       600       610       620       630       640
           -|-       -|-       -|-       -|-       -|-       -|-       -|-       -|-
      GCGGCTGCCACTCCAACCCGCTGCTGCACCTTCGCCTCCAACATGCCCTACGTGCTGCTGCCTCCTCCGTCCTCCTTCT
      *** ******************** ******* ****** *********************** ******** ******* ****
      GCGTTGCCACTCCAACCCGCTGCTGCACCTTCGCCTCCAACATGCCTACGCCTACGCCTGCTGCCTCCTCCGTCCTCCGTCT
           -|-       -|-       -|-       -|-       -|-       -|-       -|-       -|-
           570       580       590       600       610       620       630       640
```

*FIG. 3B*

```
        650       660       670       680       690       700       710       720
         -         -         -         -         -         -         -         -
ACCTTCCTCTCTCGTGATGCTCTTCGTCTACGGCGCGGGTTTTCGTGGTGGCTACGGCGCCAGTGCGCCTTGCTGCGGG
* ***** ** **************** ** ********************* ***************************
ATCTTCCGCTCTGGTGATGCTCTTCGTCTACGGCACGAGTTTTCGTGGTGGCCACGGCGCCAGTGCGCCTTGCTGCGCGG
 650       660       670       680       690       700       710       720

730       740       750       760       770       780       790       800
         -         -         -         -         -         -         -         -
GAGCTGGGCCGCTTTCCGCCCGAGGAGTCTCCGCCGGCCGTCGCGCCGTCTCTGGCCCCGGTGGGACGTGCGC
********* ***** ************** **** ******** ** ************ **** *******
GAGCTGGGCTCGTTCCGCCAGAGGAGTCTCCGCCGGCCGTCTCCTTCCTCGTCTCCGGATCCCTGGCTGGGGGCGTGCC
 730       740       750       760       770       780       790       800

810       820       830       840       850       860       870       880
         -         -         -         -         -         -         -         -
TCCGCCCGAAGGGGTGCCCGCTGCCCGGCGGCCCTGCCTCCGGAACACGGCCCTGTGCACCT
****** ********* *** ************* *************** **************** ******
CTCGCCCGCGGGGTGCCCTCCTACGGCGGGCGGCGCCCTGCCTTCTGCCTCTGCCTCTGCTTGCCCGGCCGCCCTGCCCACCT
 810       820       830       840       850       860       870       880

890       900       910       920       930       940       950       960
         -         -         -         -         -         -         -         -
TGGGTCTCATCATGGGCACCTTCACTCTCTGCTGGTTGCCCTTCTTTTCTGGCCAACGTGCTGCGGGCCCTGGGGGGCCCC
**** ****************** *** ********* **** *********** ****** ************ ***
TGGGGCTCATCATGGGAACCTTCACTCTCTGCTGGTTGCCTTTCTTTGTTGGTCAACGTGTGCGGCCCCTCGGGGGCCCC
 890       900       910       920       930       940       950       960
```

FIG. 3C

```
       970       980       990      1000      1010      1020      1030      1040
        -         -         -         -         -         -         -         -
TCTCTAGTCCCGGGCCCGGCTTTCCTTGCCCTGAACTGGTAGGTTATGCCAATTCTGCCTTCAACCCGCTCATCTACTG
***** ** * ***** ******** ***** ** ********* ********************************
TCTCTGGTGTCGGCCCCACTTTCCTCGCCCTTAACTGGCTGGGCTATGGCTGCCTTCAACCCGCTCATCTACTG
        -         -         -         -         -         -         -         -
       970       980       990      1000      1010      1020      1030      1040

1050      1060      1070      1080      1090      1100      1110      1120
        -         -         -         -         -         -         -         -
CCGCAGCCCGGACTTTCGAGGCCGCCTTCCCGGCGTCTCTTGTGCCGCTGCCCGCCGTGCCTGCCTCCGGAGCCCTGCCCG
***************** ************* ** ****** ***** * ** * *** *** ** * ***
CCGCAGCCCGGACTTTCGGAGGCCGCCTTCCCGGCCTTCCCGGCCTGCCTGCCTGCCGGAGGAGCACCTCGCCGCCTGCCTCCC
        -         -         -         -         -         -         -         -
      1050      1060      1070      1080      1090      1100      1110      1120

1130      1140      1150      1160      1170      1180      1190      1200
        -         -         -         -         -         -         -         -
CCGCCCGCCCGGCCCTCTTCCCCTCGGGCGTTCCTGCGGCCCTGACCAGCCCGCTGGCCCATGCAGAA------GCTC
* **** ** ** ****** ** *** *** ** * ***** ******* **** ***********
CGCCCCGAGCCCTCCGGGCGCCCCCACGGCCCCAGCCCAGGCGCAGCCCAGGCTTTGCCAACGGCTC
        -         -         -
      1130      1140      1190

1210      1220
        -         -
GACGGGCTTCTTGGGGAGTTTCTTAG
*********** *** ********
GACGGGGCTTCCTGCGGACTTTCTTAG
        -         -
      1200      1210
```

*FIG.3D*

NUCLEOTIDE SEQUENCES CODING FOR THE BOVINE β₃-ADRENERGIC RECEPTOR (ARβ₃) AND THEIR APPLICATIONS

This application was filed as application PCT/FR94/00447 on Apr. 21, 1994, and it entered the national stage on Feb. 21, 1995.

BACKGROUND OF INVENTION

1. Field of the Invention

The present invention relates to nucleotide sequences coding for the bovine β₃-adrenergic receptor (ARβ₃), to the use of the said sequences as probes and for the expression of peptides and/or of fragments of the latter having bovine ARβ₃ activity, to the vector which is useful for the said expression and also to host cells containing the said vector.

The present invention also relates to a method for the screening of substances possessing an agonist or antagonist action with respect to peptides of bovine origin having β₃-adrenergic receptor activity.

2. Description of the Related Art

Catecholamines such as adrenaline and noradrenaline, synthetic agonists of these catecholamines which mimic their biological functions and antagonists which block these biological functions are known to exert their effects by binding to specific recognition sites (membrane receptors) located on the cell membranes.

Two main classes of adrenergic receptors have been defined, α-adrenergic receptors and β-adrenergic receptors.

In the set of these two classes, five subtypes of catecholamine receptors are now distinguished ($α_1$-, $α_2$-, $β_1$-, $β_2$- and $β_3$-AR). Their genes have recently been isolated and identified (S. COTECCHIA et al., 1988, Proc. Natl. Acad. Sci. USA, 85, 7159–7163; B. K. KOBILKA et al., 1987, Science, 238, 650–656; T. FRIELLE et al., 1987, Proc. Natl. Acad. Sci. USA 84, 7920–7924; L. J. EMORINE et al., 1987, Proc. Natl. Acad. Sci., USA, 84, 6995–6999; L. J. EMORINE et al., 1989, Science, 245, 1118–1121). Analysis of these genes has enabled them to be recognized as belonging to a family of integral membrane receptors displaying certain homologies (R. A. F. DIXON et al., 1988, Annual Reports in Medicinal Chemistry, 221–233; L. J. EMORINE et al., 1988, Proc. NATO Adv. Res. Workshop), in particular in respect of 7 transmembrane regions which are coupled to regulatory proteins, known as G proteins, capable of binding guanosine triphosphate (GTP) molecules.

These membrane receptors, when they have bound the appropriate ligand (agonist or antagonist), undergo a change in conformation, which induces an intra-cellular signal which modifies the behaviour of the target cell.

In the case of β-adrenergic receptors, when they bind to catecholamine agonists, they catalyse the activation of a class of G proteins, which in turn stimulates adenylate cyclase activity, while ARβ antagonists act in competition with the agonists for binding to the receptor and prevent activation of adenylate cyclase.

When adenylate cyclase is activated, it catalyses the production of an intracellular mediator or second messenger, in particular cyclic AMP.

The inventors have recently demonstrated new β-adrenergic receptors in man, designated Hu-ARβ₃, and in the mouse (International Application WO 92/12,246), designated Mu-ARβ₃, and characterized by properties different from those of the $β_1$ and $β_2$ receptors, in particular in that they behave differently with respect to substances which are, respectively, $β_1$- and $β_2$-receptor antagonists and agonists (International Application WO 90/08,775).

In particular, the Hu-ARβ₃ receptor consists, more especially, of a sequence of 408 amino acids, and is considered to contain seven hydrophobic transmembrane regions separated by intra- and extracellular hydrophilic loops, and the Mu-ARβ₃ receptor consists of a sequence of 400 amino acids and also contains 7 transmembrane regions.

The previous studies relating to Hu-ARβ₃ and Mu-ARβ₃ showed, in particular, that the β₃-adrenergic receptor participates in disorders such as diabetes and/or obesity, in as much as it is expressed in tissues which play an important part in metabolism (adipose tissues, skeletal muscles in particular).

Continuing his studies along these lines, one of the inventors sought to demonstrate such a β₃-adrenergic receptor in cattle (Bo-ARβ₃), so as to be able to have available a tool for regulating the amount of fats in these animals, in particular with the object of improving the quality of the meat.

SUMMARY OF THE INVENTION

The subject of the present invention is a nucleotide sequence, characterized in that it corresponds to the cDNA of the bovine gene coding for the bovine β₃-adrenergic receptor.

According to an advantageous embodiment of the said nucleotide sequence, it comprises the nucleotide sequence and the deduced amino acid sequence (SEQ ID No. 1) of formula (I).

In this sequence, the underlined ATG which occurs at position 107 probably corresponds to the initiation codon for protein synthesis.

There is 85% homology between the bovine and human nucleotide sequences coding for the β₃-adrenergic receptor, and there is 76% homology between the bovine and murine nucleotide sequences coding for the β₃-adrenergic receptor.

The said sequence comprises, in particular, the following single restriction sites:

Bpu1102 I, Fok I, EcoR V, Bcg I, Nhe I, BspM I, Afl III, Age I, BstE II, BspH I, Bsg I, Nsp I, Nsp7524 I, NspC I, Sap I, BamH I, BstY I, Asc I, Sty I, Hinc II, Apa I, Bsp120 I, Bbe I, Ehe I, Kas I, Nar I, Ecl136 I, SaC I, Stu I, Fse I, Drd I, Tth111 I, Srf I, Bsu36 I, Sfc I, BstX I, Ase I, Bsm I, Dra I.

The subject of the invention is also the fragments of the said sequence which are useful for expression of the corresponding peptide and/or detection of the bovine gene coding for the bovine β₃-adrenergic receptor.

Among the said fragments, there may be mentioned:
- the 78-base pair fragment which corresponds to nucleotides 218–295 of the sequence of formula I and which codes for the transmembrane region TM1,
- the 72-base pair fragment which corresponds to nucleotides 332–403 of the sequence of formula I and which codes for the transmembrane region TM2,
- the 66-base pair fragment which corresponds to nucleotides 434–499 of the sequence of formula I and which codes for the transmembrane region TM3,
- the 69-base pair fragment which corresponds to nucleotides 572–640 of the sequence of formula I and which codes for the transmembrane region TM4,
- the 72-base pair fragment which corresponds to nucleotides 713–784 of the sequence of formula I and which codes for the transmembrane region TM5, the 66-base pair fragment which corresponds to nucleotides 983–1048 of the sequence of formula I and which codes for the transmembrane region TM6, the 78-base pair fragment which corresponds to nucleotides 1070–1147 of the sequence of formula I and which codes for the transmembrane region TM7.

The subject of the present invention is also cDNA clones, characterized in that they comprise a sequence fragment coding for the bovine $\beta_3$ receptor (Bo-AR$\beta_3$).

According to the invention, the clone designated M13-6.6 comprises 2979 base pairs, includes the sequence of formula I and comprises the following single restriction sites: EcoR V, Bcg I, Nhe I, BstE II, BspH I, Bsg I, Sap I, BamH I, Asc I, Stu I, Fse I, Drd I, Srf I, Sfc I, Ase I, Bsm I, Dra I, Bsp1407 I, Csp6 I, Rsa I, Ssp I, Dra III, Bgl II, Afl II, Spe I, Tfi I, Hpa I, Nde I, EcoN I, BsaB I, Pvu I.

The subject of the present invention is also nucleotide probes, characterized in that they consist of a nucleotide sequence as is defined above, or a fragment of the latter, labelled using a label such as a radioactive isotope, a suitable enzyme or a fluorochrome.

The said nucleotide probes are characterized in that they hybridize with the nucleotide sequences as are defined above but do not hybridize with the genes coding for the $\beta_1$- and $\beta_2$-adrenergic receptors, or with the messenger RNA of the said $\beta_1$- and $\beta_2$-adrenergic receptors.

According to an advantageous embodiment of the said probe, its sequence is homologous with or complementary to that of a segment of at least 10 bp of the sequence I.

BRIEF DESCRIPTION OF THE DRAWINGS

FIGS. 1a and 1b depict restriction sites contained in cloned fragments. FIG. 1a depicts restriction sites contained in the 2,000 bp fragment. FIG. 1b depicts single restriction sites contained in the 3 kb fragment.

FIGS. 2.1 and 2.2 depict the homology among the bovine $\beta_3$ peptide (BETA3 BOV; SEQ ID NO:2), the human $\beta_3$ peptide (BETA3 HU; SEQ ID NO:3), the rat $\beta_3$ peptide (BETA3 RA; SEQ ID NO:4) and the murine $\beta_3$ peptide (BETA3 MO; SEQ ID NO:5). FIG. 2.1 depicts amino acids 1–240 of the peptides. FIG. 2.2 depicts amino acids 241–405 of the bovine $\beta_3$ protein, amino acids 241–408 of the human, and amino acids 241–400 of the rat and murine proteins.

FIGS. 3.1, 3.2, 3.3, and 3.4 depict the homology between the human $\beta_3$ DNA (Hu$\beta_3$; SEQ ID NO:7) and the bovine $\beta_3$ DNA (bov $\beta_3$; SEQ ID NO:6). FIG. 3.1 depicts nucleotides 1–320. FIG. 3.2 depicts nucleotides 321–640. FIG. 3.3 depicts nucleotides 641–960. FIG. 3.4 depicts nucleotides 961–1190.

DESCRIPTION OF THE PREFERRED EMBODIMENTS

Figure 1B:
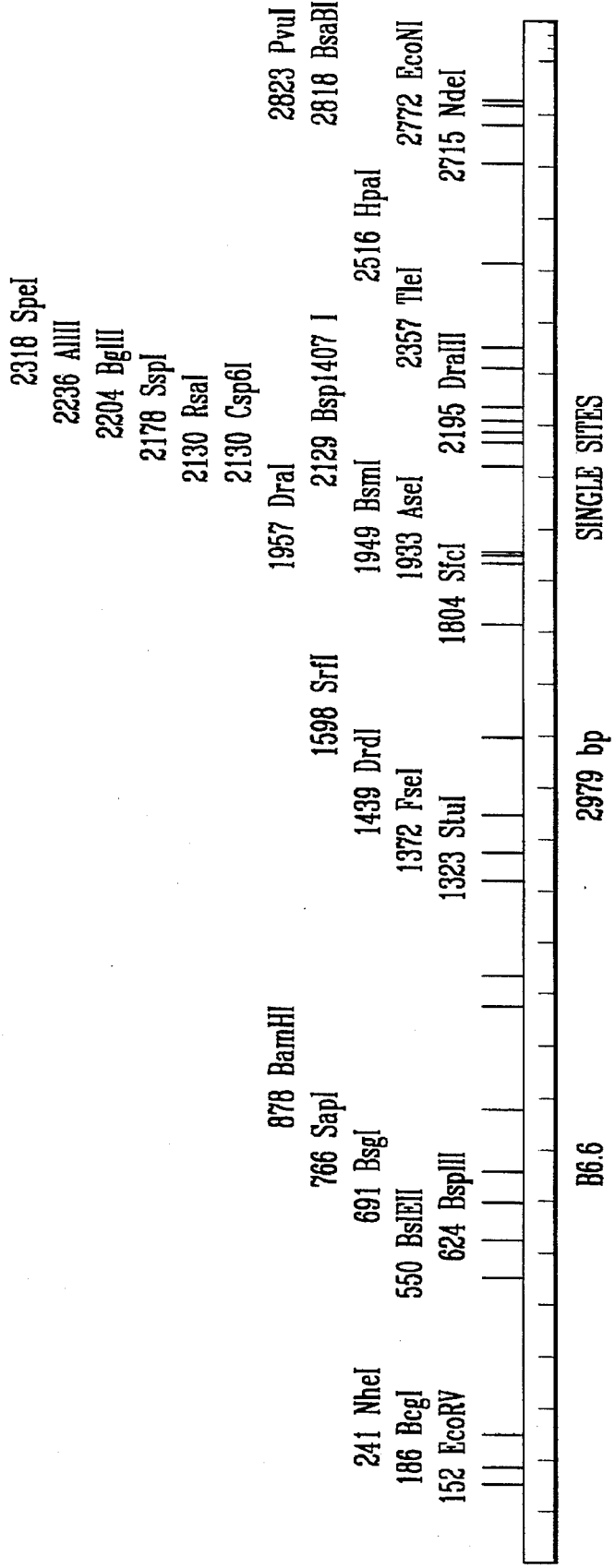

For the purpose of the present invention, "homologous sequence" encompasses not only sequences identical to the sequence I, or to a fragment of the latter, but also those which differ therefrom only by the substitution, deletion or addition of a small number of nucleotides, provided that the sequences thus modified have a specificity of hybridization equivalent to that of the sequence (I) or of the unmodified segment in question.

Likewise, "complementary sequence" is understood to mean not only sequences which are strictly complementary to the sequence (I) or to its segments, but also modified sequences, as indicated above, possessing a specificity of hybridization equivalent to that of the said strictly complementary sequences.

The hybridization conditions are defined as follows:

For the shortest probes, that is to say of approximately 10 to approximately 100 nucleotides, suitable hybridization conditions are as follows: 750 mM NaCl, 75 mM Tris-sodium citrate, 50 µg/ml salmon sperm DNA, 50 mM sodium phosphate, 1 mM sodium pyrophosphate, 100 µM ATP, 10 to 25% formamide, 1% Ficoll ("PHARMACIA", average molecular weight 400.00), 1% polyvinylpyrrolidone, 1% bovine serum albumin, for 14 to 16 h at 42° C.

For the longest probes, that is to say possessing more than approximately 100 nucleotides, suitable hybridization conditions are those stated above for the shortest probes, but in which the medium defined above contains 40% of formamide instead of 10 to 25% of formamide.

According to an advantageous arrangement of this embodiment, the said probe can be advantageously defined by any one of the above nucleotide sequences, and in particular by the 2-kbase fragment which corresponds to the whole of the sequence of formula I.

The subject of the present invention is also a peptide and/or a peptide fragment, characterized in that it is encoded by a nucleotide sequence as is defined above, and in that it displays $\beta_3$-adrenergic receptor activity.

$\beta_3$-Adrenergic receptor activity is that defined in French Patent Application No. 89/00,918, namely that, when the fragment is exposed at the surface of a cell, it is capable of participating in the activation of adenylate cyclase in the presence of one of the following agonists: BRL 28410, BRL 37344, CGP 12177A, (1)-isoproterenol and carazolol; or, it is capable of being recognized by antibodies which do not recognize either the $\beta_1$-adrenergic receptor or the $\beta_2$-adrenergic receptor; or, it is capable of generating antibodies which do not recognize either the $\beta_1$ receptor or the $\beta_2$ receptor.

According to an advantageous embodiment of the said peptide, it comprises 405 amino acids and possesses the amino acid sequence (SEQ ID No. 2) of formula II:

This peptide is designated hereinafter bovine $\beta_3$-adrenergic receptor (Bo-AR$\beta_3$).

The invention also comprises the peptides which are variants of those defined above, which contain certain mutations, without the peptides losing the $\beta_3$-adrenergic receptor properties.

Among these variants, there may be mentioned those which are recognized by antibodies that recognize the transmembrane regions, as well as those which are recognized by antibodies that recognize the regions other than the transmembrane regions.

The subject of the present invention is also fragments or combinations of fragments of Bo-AR$\beta_3$, according to the invention, and in particular:

a fragment of 26 amino acids corresponding to the segment 38–63 of the formula II and constituting the transmembrane region TM1, a fragment of 24 amino acids corresponding to the segment 76–99 of the formula II and constituting the transmembrane region TM2, a fragment of 22 amino acids corresponding to the segment 110–131 of the formula II and constituting the transmembrane region TM3, a fragment of 23 amino acids corresponding to the segment 156–178 of the formula II and constituting the transmembrane region TM4, a fragment of 24 amino acids corresponding to the segment 203–226 of the formula II and constituting the transmembrane region TM5, a fragment of 22 amino acids corresponding to the segment 293–314 of the formula II and constituting the transmembrane region TM6, a fragment of 26 amino acids corresponding to the segment 322–347 of the formula II and constituting the transmembrane region TM7.

The said fragments may advantageously be obtained by synthesis, in particular by the Merrifield method.

The subject of the present invention is also a recombinant cloning and/or expression vector, characterized in that it comprises a nucleotide sequence according to the invention.

For the purpose of the present invention, recombinant vector is understood to mean either a plasmid, a cosmid or a phage.

According to an advantageous embodiment of the said vector, it consists of a suitable recombinant vector comprising, in particular, an origin of replication in a suitable host microorganism, in particular a bacterium or a eukaryotic cell, at least one gene whose expression permits selection either of the bacteria or of the eukaryotic cells which have received the said vector, and a suitable regulatory sequence, in particular a promoter permitting expression of the genes in the said bacteria or eukaryotic cells, into which vector is inserted a nucleotide sequence or a sequence fragment as are defined above, which vector is a vector for the expression of a peptide, of a peptide fragment or of a combination of peptide fragments having bovine $\beta_3$-adrenergic receptor activity.

According to an advantageous arrangement of this embodiment, the said vector consists of an expression vector pRc/CMV into which is inserted, in the multisite linker, at least the fragment coding for the bovine $\beta_3$-adrenergic receptor; such a plasmid has been designated pRc/CMV-Bo$\beta$3-ADR, and has been deposited with the Collection Nationale de Cultures de Microorganismes [National Collection of Microorganism Cultures] (CNCM) held by the PASTEUR INSTITUTE, dated 15th Apr. 1993, under No. I-1297.

The subject of the present invention is also a suitable host cell obtained by genetic transformation, characterized in that it is transformed with an expression vector according to the invention.

Such a cell is capable of expressing a peptide of bovine origin having $\beta_3$-adrenergic receptor acitivity.

According to an advantageous embodiment, the host cell consists, in particular, of cells of the CHO (Chinese Hamster Ovary) line.

Another of the microorganisms used can consist of a bacterium, in particular *Escherichia coli*.

It was not obvious that cattle have $\beta_3$-adrenergic receptors whose activation unexpectedly enables the amount and quality of the fats to be regulated, thereby enabling the quality of bovine meat to be improved.

Advantageously, the bovine $\beta_3$-adrenergic receptors according to the invention constitute a tool for the selection of ligands participating in the activation of these receptors, and make it possible to identify and select $\beta$-adrenergic ligands which are specific for the $\beta_3$-adrenergic receptors, and especially ligands having more affinity and which are more selective for the bovine $\beta_3$-adrenergic receptor than for the human $\beta_3$-adrenergic receptor.

According to the invention, the method for the selection and identification of substances capable of behaving as a specific ligand with respect to a peptide (bovine $\beta_3$-adrenergic receptor) according to the invention comprises:

bringing the said substance into contact with a host cell previously transformed with an expression vector as defined above, which host cell expresses the said bovine peptide (bovine $\beta_3$-adrenergic receptor), if necessary after suitable physical or chemical induction, and which contacting is carried out under conditions permitting the formation of a bond between at least one of the specific sites and the said substance if circumstances are appropriate, and detecting the possible formation of a complex of the ligand-peptide type.

Such a process makes it possible to select either ligands specific for the $\beta_3$-adrenergic receptor, or ligands specific for the bovine $\beta_3$-adrenergic receptor exclusively.

Besides the foregoing arrangements, the invention also comprises other arrangements which will become apparent from the description which follows, reference being made to the attached drawings wherein:

It should, however, be clearly understood that these examples are given only by way of illustration of the subject of the invention, and in no way constitute a limitation thereof.

EXAMPLE 1

Isolation and Identification of the Bovine $\beta_3$-Adrenergic Gene

Preparation of RNA

The bovine $\beta_3$-adrenergic gene was isolated from a cDNA library of calf brown adipose tissue, constructed in bacteriaphage $\lambda$gt11.

To this end, the total RNA is extracted from calf brown adipose tissue by the guanidinium thiocyanate method, and the poly(A)$^+$ messenger RNA is then purified using oligo (dT) columns (Pharmacia Ref.: 27-9258-01).

The total RNA and messenger RNA were analysed by Northern blotting to verify the presence and size of the messengers of the desired gene. After electrophoresis, the RNA was transferred onto a positively charged nylon membrane (Amersham Hybond®-N+ ref. RPN 203B). This membrane is then hybridized with a radiolabelled probe (radiolabelling: see screening of recombinant phages, below), consisting of a 2900-base pair DNA fragment containing the whole of the murine $\beta_3$-adrenergic gene previously isolated in the laboratory (NAHMIAS et al., 1991, EMBO J., 10, 3721–3727; International Application WO 92/12,246). After hybridization with the radiolabelled probe, the filters are washed and exposed for several days to autoradiography film (KODAK X-OMAT AR); an approximately 2.0-kilobase fragment is observed, both in the total RNA fraction and in the purified messenger RNA fraction. This confirms that the gene corresponding to the $\beta_3$-adrenergic receptor is expressed in calf brown adipose tissue, and that the cDNA library can be constructed from this purified poly(A)$^+$ messenger RNA.

To verify that the RNA source is indeed brown adipose tissue, the Northern blot obtained above was hybridized with a radiolabelled probe corresponding to the gene for human uncoupling protein (hUCP). This protein is only present in this type of adipose tissue, and may be regarded as a kind of "marker" for brown adipose tissue. With this probe, a strongly positive signal is detected.

Synthesis of cDNA

The corresponding cDNA is then synthesized, taking as template the purified poly(A)+ messenger RNA and as primer for the synthesis of the first strand an oligo(dT)$_{15}$ primer originating from the "RiboClone cDNA synthesis system" kit (Promega ref. C 2100). The synthesis of the first cDNA strand takes place in the presence of AMV reverse transcriptase, and the synthesis of the second strand is carried out using two enzymes acting simultaneously (*E. coli* polymerase I and *E. coli* RNase H). The double-stranded cDNA is then treated with T4 DNA polymerase so as to obtain blunt ends. The Promega C 2100 kit is used for all of these reactions.

Next, adaptors containing EcoR I sites are added so as to be able to insert the cDNA obtained into bacteriaphage λgt11 under the following conditions, described in the EcoR I Adaptor Ligation System I kit (Promega ref. C 1900):

the cDNA is centrifuged through a Sephacryl® S-400 matrix (kit) to remove small molecules; the adaptors are then added to the cDNA by ligation in the presence of T4 DNA ligase, the mixture is left overnight and a second centrifugation is performed through a Sephacryl® S-400 column so as to remove unbound adaptors.

Before inserting the cDNA thus treated into the λgt11 vector, the adaptors are phosphorylated in the presence of T4 polynucleotide kinase.

Insertion of the cDNA into Bacteriaphage λgt11

The bacteriaphage λgt11 used as vector originates from the "Protoclone Lambda gt11 System" kit Promega ref. T 301/0-2). The DNA of the phage is digested with EcoR I and dephosphorylated. Dephosphorylation prevents the vector from closing up again.

Several ligations are performed with variable amounts of the cDNA obtained, with 0.5 μg of vector DNA, under the following conditions, for each ligation: for 3 hours at room temperature in the presence of T4 DNA ligase (Promega kit C1900).

An in vitro encapsidation is then performed using the "Packagene" extracts present in Promega kit T301/0-2.

After incubation at 22° C. for 2 hours, the reconstituted phage particles are used to infect bacteria, in particular the strain Y1090(r–) (Genotype: Δ(lacU169), proA+, Δ(lon), araD139, strA, supF, (trpC22::Tn10), (pMC9), hsd(r–, m+)), under the following conditions: the encapsidated phages are very greatly diluted (1/1,000 or 1/10,000); each dilution of phages is incubated with Y1090(r–) cells at 37° C. for 30 minutes, and these infected bacteria are then plated out on a nutrient medium (LB agar) contained in Petri dishes. The dishes are incubated overnight at 37° C., and the next day lytic plaques are observed; each plaque corresponds to a recombinant phage. By counting the number of lytic plaques and multiplying by the given dilution factor, the titer of the cDNA library is determined, and is approximately 4 million recombinant phages. The background of the vector alone without insert is 3.5%, which is entirely acceptable.

Screening of Recombinant Phages

On the basis of the results obtained, approximately 200,000 phages were plated out on Petri dishes (LB agar medium) so as to be able to screen them with a radiolabelled probe under the following conditions:

bacterial strain used: LE 392 (Genotype: F–, hsdR 574 (r–, m+), supE44, supF58, lacY1 or Δ(lacIZY)6, galK2, galT22, metB1, trpR55, λ–);

probe: 2900-base pair DNA fragment (murine β$_3$-adrenergic gene), as specified above for Northern blotting, radiolabelled by random priming (Boehringer kit ref. 1004 760), incorporating 50 μCi of [α-$^{32}$P]dATP and 50 μCi of [α-$^{32}$P]dCTP (Amersham references PB 10204 and PB 10205).

After transfer of the DNA from the lytic plaques onto Hybond®-N+ membranes (Amersham ref. RPN 132B), the latter are hybridized with the radiolabelled probe, then washed and exposed overnight to autoradiography film.

17 hybridization signals were observed, 11 of which subsequently proved to be false positives. The 6 remaining clones (1, 3, 5, 6, 8 and 9) were purified by four successive isolations, followed by a hybridization with the murine β$_3$-adrenergic probe described above.

Analysis of Positive Clones

To identify the clone(s) containing the entire bovine β$_3$-adrenergic gene, that is to say the cDNA corresponding to the coding region for the whole protein, 2 methods were used: amplification by PCR and cleavage with a restriction endonuclease, with the object of finding among the positive clones the one which contains the largest insert.

1) Amplification by PCR was carried out in lysate of phages (encapsidated phage particles) using the following two primers:

1218: 24-mer λgt11 primer (sense strand) of formula: 5' d(GGTGGCGACGACTCCTGGAGCCCG)3' (SEQ. ID NO:8), and 1222: λgt11 primer (antisense strand), also 24-mer, of formula: 5' d(TTGACACCAGACCAACTGGTAATG)3' (SEQ ID NO:9) (New England Biolabs).

In view of the fact that these primers hybridize on both sides of the insertion site of the cDNA into the phage, it was possible in this way to find out the size of the fragments inserted into the different positive clones.

2) The DNA of the 6 phages of interest was prepared and cut with the restriction enzyme EcoR I so as to verify the size of the inserts; hybridization with the murine β$_3$-adrenergic probe enabled the clone containing the largest positive insert to be detected.

The outcome of these two approaches was that clone No. 6 was chosen for a more exhaustive analysis in view of the fact that it contains the largest insert of desired cDNA (3 kilobases).

After cleavage of the phage λ with the restriction enzyme EcoR I, the fragment containing cDNA was inserted into bacteriophage M13tg131 so as to be able to sequence the gene.

EXAMPLE 2

Sequencing of the Bovine β$_3$-Adrenergic Gene

The approximately 3-kb DNA fragment bounded by the EcoR I enzyme sites was sequenced.

This DNA fragment was purified from the DNA of clone 6 and subcloned into the EcoR I site of the vector M13tg131. The M13 clones which had integrated the DNA fragment in the 2 opposing orientations (6.3 and 6.6) were identified and sequenced.

To perform the sequencing reactions, the USB Sequenase Version 2.0 kit (United States Biochemical ref. 70770) was used.

The sequence was produced using specific primers, which hybridize with the sense strand (clone M13-6.6) or with the antisense strand (clone M13-6.3) according to the method of Sanger (MANIATIS et al., *Molecular Cloning*, 2nd edition, pages 13.3–13.10).

The results obtained from the sequence of the 3-kilobase EcoR I fragment show the nucleotide sequence of bovine ARβ$_3$ (1215 bp) and non-coding regions (106 bp at the 5' end and 638 bp at the 3' end) (formula I). The restriction sites contained in the 2,000-bp fragment are positioned on FIG. 1a (bov 6.6 short (pA)).

FIG. 1b shows the single restriction sites contained in the 3-kb fragment which was sequenced.

Comparison of the coding regions of the human and bovine β$_3$ genes (FIG. 3) shows a strong homology (85% in respect of the nucleotide sequences between bovine and human AR; comparison of the coding regions of the bovine and murine β$_3$ genes also shows strong homology (76% in respect of the nucleotide sequences between bovine AR and murine AR).

The bovine β$_3$ gene codes for the peptide of 405 amino acids which displays a very large homology with the human β$_3$ peptide or the murine β$_3$ peptide (FIG. 2), as indicated above.

EXAMPLE 3

Construction of a vector for the Expression of Bovine ARβ$_3$

Figure 4:
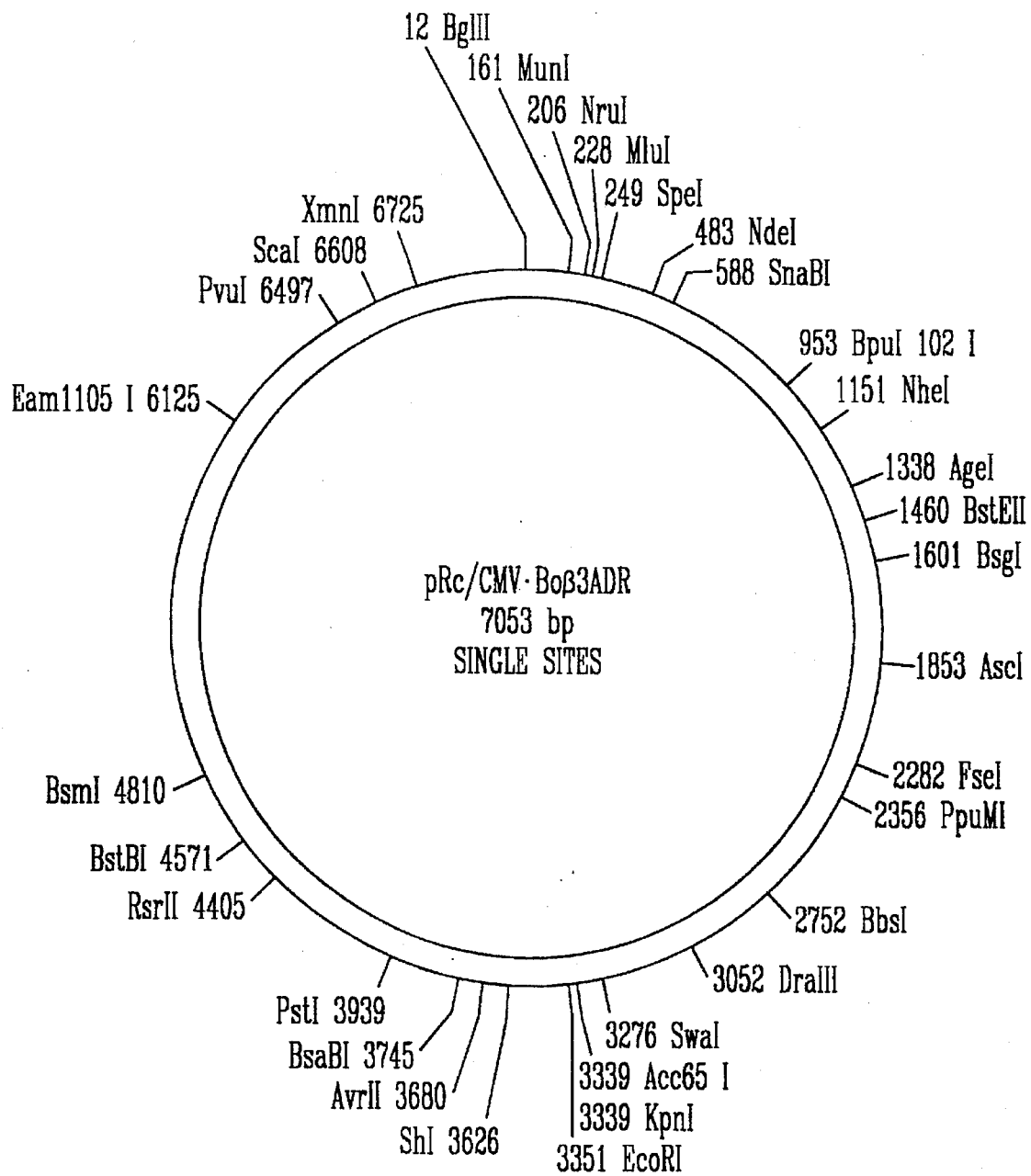
FIG. 4 depicts a schematic of pRc/CMV-Bo$\beta_3$-ADR.

The restriction map of the 2-kb fragment which was sequenced (FIG. 1a) shows the presence of a site of cleavage by the enzyme Srf I at position 1598, that is to say 270 nucleotides upstream of the coding region of the bovine β$_3$ gene. DNA of the clone M13-6.6 was digested with the enzymes EcoR I and Srf I to liberate the 1598-base pair fragment containing the coding region of the bovine β$_3$ gene and a portion of the untranslated 3' region. This DNA fragment was purified and then inserted into the expression vector pRc/CMV at the Hind III and Xba I cleavage sites (FIG. 4).

Since the ends generated by the enzymes Hind III and Xba I on the one hand, and EcoR I and Srf I on the other hand, are not compatible, care was taken to treat the EcoR I and Srf I ends of the insert on the one hand with the Klenow fragment of polymerase I, and the Hind III and Xba I ends of the vector on the other hand with the Klenow fragment of polymerase I, so as to obtain blunt ends (MANIATIS et al., *Molecular Cloning*, 2nd edition, pages 5.40–5.42).

Figure 5:
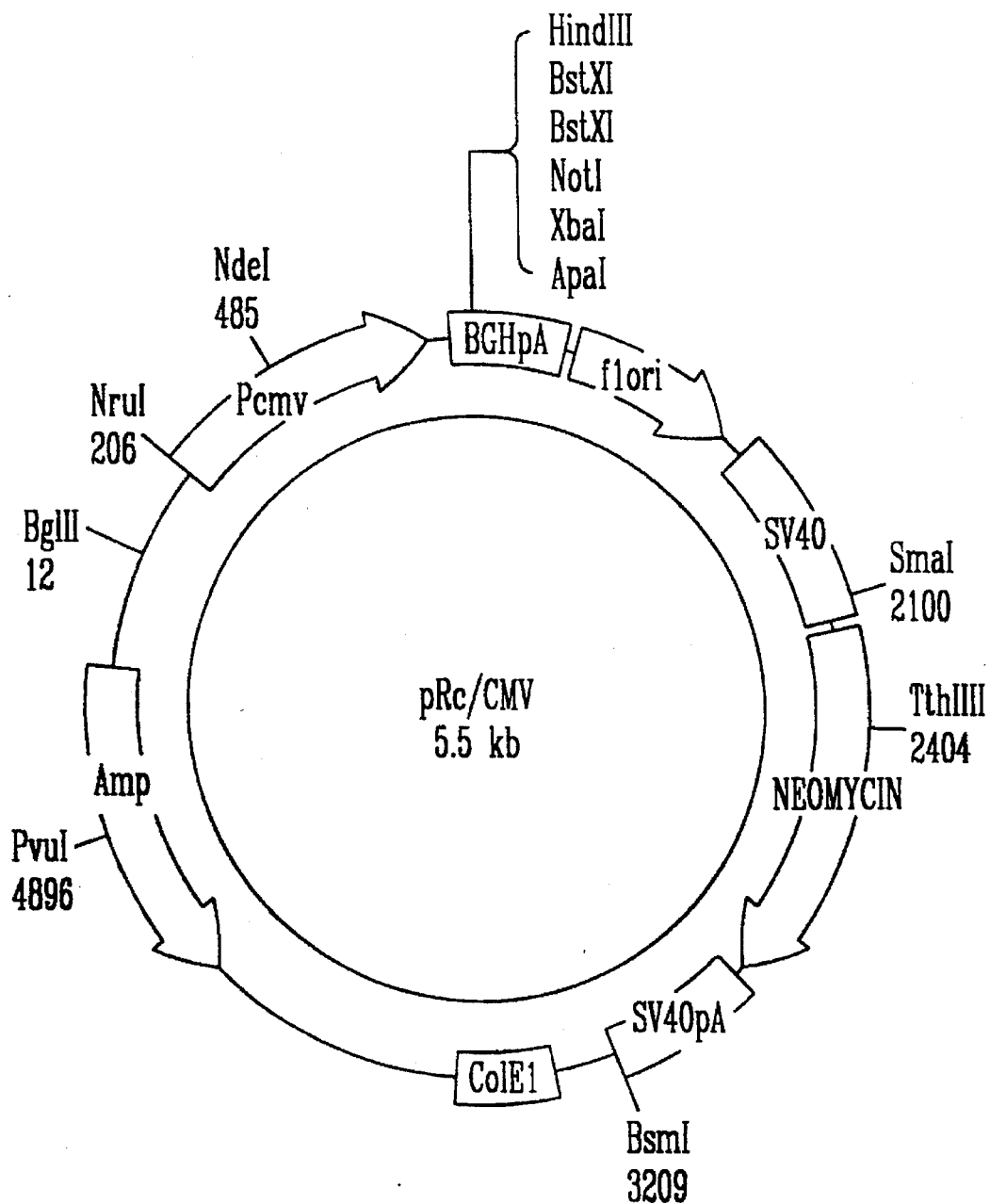
FIG. 5 depicts a schematic of pRc/CMV, including a multisite linker comprising the following single restriction sites; Hind III, BstX I, Not I, Xba I and Apa I.

The recombinant plasmid pRc/CMV-Boβ3-ADR shown in FIG. 5 was thereby obtained.

EXAMPLE 4

Pharmacological Properties of the Expression Product of the Bovine β$_3$ Gene a) Transfection of CHO-K1 Cells To characterize better the bovine β$_3$-adrenergic receptor, the bovine β$_3$ gene is expressed at the surface of eukaryotic cells, which possess all the elements needed for transduction of the signal.

The recombinant plasmid pRc/CMV of Example 3 was transfected into CHO-K1 cells by a lypofectin transfection method; the transfected cells are selected with G418 (neomycin derivative).

More specifically, the said transfection method is carried out as follows:

CHO-K1 cells (ATCC CCL 61) are cultured to confluence in a culture medium containing; 45% DMEM medium, 45% F12-Ham medium, 10% heat-inactivated foetal calf serum, 2 mM glutamine, 100 U/ml penicillin and 100 µg/ml streptomycin.

1 µg of DNA of bovine β$_3$ plasmid pRc/CMV is mixed with 5 µl of lipofectin (Gibco) and 1,000 µl of the above-mentioned culture medium without serum.

This mixture is added to cells in culture, which are left to incubate at 37° C. for 5 hours.

The medium is replaced with a culture medium, mentioned above, containing serum, and the cells are incubated again at 37° C. for 48 hours. The cells are then distributed in 96 wells according to variable dilutions and incubated in the presence of geneticin (G418, Gibco) at a concentration of 400 µg/ml in complete medium for approximately 10 days, the medium being changed every other day.

The different colonies obtained are then subcloned, first in 48 wells and then in 6 wells, before screening.

Stable colonies are screened for their capacity to bind specifically to [$^{125}$I]cyanopindolol and also for their capacity to stimulate adenylate cyclase in the presence of isoproterenol, in accordance with protocol described in TATE et al., Eur. J. Biochem., 191, 196, 357–361.

Transfected cells stably expressing ARβ$_3$ bind [$^{125}$I] cyanopindolol with an affinity equivalent to that of the corresponding ARβ$_3$ in man or in mouse and also obtained by cloning.

A set of subclones were selected from the stable clones; one of them, designated 62-26, was used for the pharmacological evaluation of bovine ARβ$_3$.

b) Pharmacological Characteristics of the Bovine ARβ$_3$ Receptor

Pharmacological characterization of the bovine ARβ$_3$ receptor was carried out using the stable clones 62-26. The pharmacological properties of 10 β$_3$-adrenergic ligands were determined by studies of stimulation of adenylate cyclase and of binding of [$^{125}$I]cyanopindolol.

Adenylate cyclase activation experiments were carried out according to the protocol detailed in BLIN et al., Mol. Pharmacol., 1991, 44, 1094–1104.

Briefly, preconfluent cells in six-well plates (0.6×10$^6$ cells/well) are placed in contact or otherwise with increasing doses of ligands for 30 minutes at 37° C. Reaction is stopped by washing in PBS at 4° C. and adding 500 µl of 1N NaOH. After centrifugation and neutralization with 1N acetic acid, the cell lysates are recovered and the total amount of cAMP accumulated is determined using a commercial assay kit.

Study of the competitive binding of ligands was carried out on intact cells according to the protocol detailed in BLIN et al., Mol. Pharmacol., 1991, 44, 1094–1104. Briefly, 10$^5$ cells are incubated with 0.5 nM [$^{125}$I]cyanopindolol in the presence or absence of increasing concentrations of competitors for 30 minutes at 37° C. Reaction is stopped by dilution with ice-cold PBS, the cells are filtered off and the radioactivity is measured in a gamma counter. The results were analysed using Graph-Pad© software.

Among the ligands tested, four are described as β$_1$-, β$_2$- and β$_3$-AR-receptor agonists: (−)-iso-proterenol, (−)-epinephrine, (−)-norepinephrine, BRL 37344; three are described as specific for the ARβ$_3$ receptor (β$_1$-, β$_2$-AR antagonists): CGP12177A, ICI201651, bucindolol. Bupranolol was also tested since it is described as an antagonist of the three subtypes of receptor (BLIN et al., Br. J. Pharmacol., 1994, in press). Lastly, (−)-propranolol, described as a partial agonist of the human ARβ$_3$ receptor and antagonist of the mouse ARβ$_3$ receptor (NAHMIAS et al., EMBO J., 1991, 10, 3721–3727), was tested.

The values of the adenylate cyclase activation constants (K$_{act}$), of the inhibition constants (K$_i$) and of the intrinsic activity (IA) corresponding to the ratio of the effect of the ligand at 10$^{-4}$M to the effect of isoproterenol at 10$^{-4}$M, which are obtained for the different ligands, are presented in the table below. The four ligands which are agonists of the three subtypes of receptors ($\beta_1$-, $\beta_2$-, $\beta_3$-AR) have $K_{act}$ and $K_i$ values close to those obtained for the human AR$\beta_3$ receptor (BLIN et al., Br. J. Pharmacol., 1994, in press), mouse AR$\beta_3$ receptor (NAHMIAS et al., EMBO J., 1991, 10, 3721–3727) and rat AR$\beta_3$ receptor (GRANNEMAN et al., J. Pharmacol. Exp. Therap., 1991, 40, 895–899; MUZZIN et al., J. Biol. Chem., 1991, 266, 24053–24058).

The specific ligands for the AR$\beta_3$ receptor all have a smaller $K_{act}$ value for the bovine AR$\beta_3$ receptor compared to the human and mouse AR$\beta_3$ receptors, and hence improved efficacy in stimulating adenylate cyclase. (–)-Propranolol is a partial agonist at bovine AR$\beta_3$, as for the human AR$\beta_3$ receptor. In contrast, bupranolol, which is described as a potent antagonist for human and murine AR$\beta_3$ receptors, is a partial agonist at the bovine AR$\beta_3$ receptor.

| | Mouse RA$\beta$3-CHO | | | Human RA$\beta$3-CHO | | | Bovine RA$\beta$3-CHO | | |
|---|---|---|---|---|---|---|---|---|---|
| LIGANDS | Binding Ki (nM) | Accumul. Kact (nM) | cAMP IA | Binding Ki (nM) | Accumul. Kact (nM) | cAMP IA | Binding Ki (nM) | Accumul. Kact (nM) | cAMP IA |
| agonists $\beta1/\beta2/\beta3$ | | | | | | | | | |
| (-) isproterenol | — | 99 ± 44 | 1.4 ± 0.1 | 620 | 4 | 0.9 | 84 ± 81 | 14 ± 2 | 0.9 ± 0.1 |
| (–) epinephrine | 4,600 ± 1,850 | 23 ± 0.3 | 0.91 ± 0.03 | 20,650 ± 2.810 | 49 ± 5 | 1.00 ± 0.04 | 11,105 ± 7.345 | 50.7 ± 3.7 | 0.8 ± 0.3 |
| (-) norepinephrine | 1,840 ± 600 | 13 ± 4 | 1.06 ± 0.06 | 475 ± 75 | 6.32 ± 0.7 | 1.00 | 423 ± 255 | 54 ± 4.3 | 1.00 ± 0.5 |
| BRL 37344 | 290 ± 136 | 0.4 ± 0.1 | 1.07 ± 0.08 | 287 ± 92 | 15 ± 3 | 1.11 ± 0.12 | 2.13 ± 1.4 | 0.3 ± 0.07 | 0.84 ± 0.1 |
| $\beta1/\beta2$ antagonists/ $\beta3$ agonists | | | | | | | | | |
| CGP 12177A | 152 ± 19 | 41 ± 9 | 0.75 ± 0.08 | 88 ± 22 | 139 ± 44 | 0.68 ± 0.02 | 218 ± 161 | 1.41 ± 0.5 | 0.93 ± 0.20 |
| ICI 201651 | 239 ± 104 | 15 ± 1 | 1.02 ± 0.02 | 85 ± 12 | 20 ± 9 | 1.14 ± 0.14 | 27.7 ± 24 | 1.1 ± 0.9 | 0.85 ± 0.1 |
| Bucindolol | 21 ± 5 | 40 ± 14 | 1.11 ± 0.06 | 23 ± 10 | 7.0 ± 1.2 | 1.01 ± 0.10 | 73 ± 42 | 12.8 ± 5.0 | 0.99 ± 0.10 |
| partial agonist/ antagonist | | | | | | | | | |
| (–) propranolol | 150 ± 22 | antagonist 406 ± 98 | — | 145 ± 8 | 1,490 ± 5500 | .51 ± 0.12 | 589 ± 74 | 661 ± 78 | 0.71 ± 0.08 |
| antagonists $\beta1/\beta2/\beta3$ | | | | | | | | | |
| (-) bupranolol | 42 ± 19 | antagonist 12 ± 1 | — | 50 ± 14 | antagonist | — | 85 ± 40 | 507 ± 75 | 0.34 ± 0.01 |

As emerges from the foregoing, the invention is in no way limited to those of its embodiments and modes of implementation and application which have just been described more explicitly; it encompasses, on the contrary, all variants which may occur to the specialist in the field, without departure from the scope or range of the present invention.

We claim:

1. An isolated and purified nucleotide sequence encoding a bovine β3-adrenergic receptor comprising SEQ ID NO:1.

2. A recombinant plasmid, comprising the nucleotide sequence according to claim 1.

3. The recombinant plasmid according to claim 2, further comprising an origin of replication for replication in a host cell, at least one gene whose expression permits selection of said host cell transformed with said plasmid, and a regulatory sequence, including a promoter permitting expression of a protein having a bovine β3-adrenergic receptor activity in said host cell.

4. The recombinant plasmid according to claim 3, wherein said plasmid is pRc/CMV-Boβ3-ADR and, wherein said plasmid is deposited with the Collection Nationale de Cultures de Microorganismes (CNCM) held by the PASTEUR INSTITUTE, dated 15th Apr. 1993, under No. I-1297.

5. A host cell transformed by a recombinant plasmid according to claim 3.

6. The transformed host cell according to claim 5, wherein said host cell is a CHO cell.

7. The transformed host cell according to claim 5, wherein said host cell is *Escherichia coli*.

8. An isolated and purified nucleic acid sequence consisting of a 72-base pair segment which corresponds to nucleotides 332–403 of SEQ ID NO:1.

9. An isolated and purified nucleic acid sequence consisting of a 69-base pair segment which corresponds to nucleotides 572–640 of SEQ ID NO:1.

10. An isolated and purified nucleic acid sequence consisting of a 66-base pair segment which corresponds to nucleotides 983–1048 of SEQ ID NO:1.

11. An isolated and purified nucleic acid sequence consisting of a 78-base pair segment which corresponds to nucleotides 1070–1177 of SEQ ID NO:1.

12. An isolated and purified protein, wherein the protein displays β3-adrenergic receptor activity and comprises SEQ ID NO:2.

13. A method for detecting the binding of an agonist or antagonist to a protein according to claim 12, comprising the steps of:

contacting said agonist or antagonist with a host cell previously transformed by a vector encoding said protein and wherein said host cell expresses said protein on its surface, under conditions permitting binding between the protein and said agonist or antagonist and detecting a complex formed between said antagonist or agonist and said protein.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2000 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 107..1321
        ( D ) OTHER INFORMATION: /function="BOVINE BETA-3 RECEPTOR"
          / product= "ADRENERGIC, BETA RECEPTOR"

( x i ) SEQUENCE DESCRIPTION: SEQ ID NO:1:

-continued

| | |
|---|---|
| CCCAGGCCAG GGAAATCGCT CCCACGCCCC GATGCCCCCG CCGCTGAGCA GGGTGAGCTG | 60 |
| GGAGACCCTT TCCCTCATTC CTTCCCGCCC CACGCGCGAC GCGGGG ATG GCT CCG | 115 |
|                                                                                    Met Ala Pro<br>                                                                                        1 | |
| TGG CCT CCT GGG AAC AGC TCT CTG ACC CCG TGG CCA GAT ATC CCC ACC<br>Trp Pro Pro Gly Asn Ser Ser Leu Thr Pro Trp Pro Asp Ile Pro Thr<br>    5                      10                  15 | 163 |
| CTG GCA CCC AAT ACT GCC AAC GCG AGT GGG CTG CCA GGG GTG CCC TGG<br>Leu Ala Pro Asn Thr Ala Asn Ala Ser Gly Leu Pro Gly Val Pro Trp<br>20                   25                     30                     35 | 211 |
| GCG GTG GCG CTG GCG GGG GCG CTG TTG GCG CTA GCG GTG CTG GCC ACC<br>Ala Val Ala Leu Ala Gly Ala Leu Leu Ala Leu Ala Val Leu Ala Thr<br>                40                     45                          50 | 259 |
| GTG GGA GGC AAC CTG CTG GTA ATC GTG GCC ATC GCC CGG ACG CCG AGA<br>Val Gly Gly Asn Leu Leu Val Ile Val Ala Ile Ala Arg Thr Pro Arg<br>            55                         60                          65 | 307 |
| CTC CAG ACC ATG ACC AAC GTG TTC GTG ACT TCG CTG GCC ACA GCC GAC<br>Leu Gln Thr Met Thr Asn Val Phe Val Thr Ser Leu Ala Thr Ala Asp<br>                70                     75                          80 | 355 |
| CTG GTG GTG GGG CTC CTG GTC GTG CCC CCG GGG GCC ACG TTG GCG CTG<br>Leu Val Val Gly Leu Leu Val Val Pro Pro Gly Ala Thr Leu Ala Leu<br>85                   90                     95 | 403 |
| ACC GGC CAC TGG CCC CTG GGC GTC ACC GGT TGC GAG CTG TGG ACC TCA<br>Thr Gly His Trp Pro Leu Gly Val Thr Gly Cys Glu Leu Trp Thr Ser<br>100                   105                    110                 115 | 451 |
| GTG GAC GTG CTG TGT GTG ACC GCC AGC ATC GAA ACC CTG TGC GCC CTG<br>Val Asp Val Leu Cys Val Thr Ala Ser Ile Glu Thr Leu Cys Ala Leu<br>                120                    125                    130 | 499 |
| GCG GTG GAC CGC TAC CTG GCC GTG ACC AAC CCG CTG CGC TAC GGC GCG<br>Ala Val Asp Arg Tyr Leu Ala Val Thr Asn Pro Leu Arg Tyr Gly Ala<br>            135                    140                    145 | 547 |
| CTG GTC ACC AAA CGC CGC GCC CTA GCA GCC GTG GTC CTG GTG TGG GTG<br>Leu Val Thr Lys Arg Arg Ala Leu Ala Ala Val Val Leu Val Trp Val<br>        150                    155                    160 | 595 |
| GTG TCC GCC GCG GTG TCG TTT GCG CCC ATC ATG AGC AAA TGG TGG CGC<br>Val Ser Ala Ala Val Ser Phe Ala Pro Ile Met Ser Lys Trp Trp Arg<br>165                   170                    175 | 643 |
| ATC GGG GCC GAT GCC GAG GCG CAG CGT TGC CAC TCC AAC CCG CGC TGC<br>Ile Gly Ala Asp Ala Glu Ala Gln Arg Cys His Ser Asn Pro Arg Cys<br>180                   185                    190                 195 | 691 |
| TGC ACC TTC GCC TCC AAC ATG CCC TAC GCG CTG CTC TCC TCC TCG GTC<br>Cys Thr Phe Ala Ser Asn Met Pro Tyr Ala Leu Leu Ser Ser Ser Val<br>                200                    205                    210 | 739 |
| TCG TTC TAT CTT CCG CTC CTG GTG ATG CTC TTC GTC TAC GCA CGA GTT<br>Ser Phe Tyr Leu Pro Leu Leu Val Met Leu Phe Val Tyr Ala Arg Val<br>            215                    220                    225 | 787 |
| TTC GTG GTG GCC ACG CGC CAG CTG CGC TTG CTG CGC GGG AGC TG GGT<br>Phe Val Val Ala Thr Arg Gln Leu Arg Leu Leu Arg Arg Glu Leu Gly<br>        230                    235                    240 | 835 |
| CGC TTC CCG CCA GAG GAG TCT CCG CCG GCT CCT TCT CGC TCC GGA TCC<br>Arg Phe Pro Pro Glu Glu Ser Pro Pro Ala Pro Ser Arg Ser Gly Ser<br>245                   250                    255 | 883 |
| CCT GGC CTG GCG GGG CCG TGC GCC TCG CCC GCG GGG GTG CCC TCC TAC<br>Pro Gly Leu Ala Gly Pro Cys Ala Ser Pro Ala Gly Val Pro Ser Tyr<br>260                   265                    270                 275 | 931 |
| GGC CGG CGG CCG GCG CGC CTT CTG CCT CTG CGG GAA CAC CGC GCC CTG<br>Gly Arg Arg Pro Ala Arg Leu Leu Pro Leu Arg Glu His Arg Ala Leu<br>        280                    285                    290 | 979 |

-continued

| | | | | | | | | | | | | | | | | |
|---|---|---|---|---|---|---|---|---|---|---|---|---|---|---|---|---|
| CGC | ACC | TTG | GGG | CTC | ATC | ATG | GGA | ACC | TTC | ACT | CTC | TGC | TGG | TTG | CCT | 1027 |
| Arg | Thr | Leu | Gly 295 | Leu | Ile | Met | Gly | Thr 300 | Phe | Thr | Leu | Cys | Trp 305 | Leu | Pro | |
| TTC | TTT | GTG | GTC | AAC | GTG | GTG | CGC | GCC | CTC | GGG | GGC | CCC | TCT | CTG | GTG | 1075 |
| Phe | Phe | Val 310 | Val | Asn | Val | Val | Arg 315 | Ala | Leu | Gly | Gly | Pro 320 | Ser | Leu | Val | |
| TCC | GGC | CCC | ACT | TTC | CTC | GCC | CTT | AAC | TGG | CTG | GGC | TAT | GCC | AAC | TCT | 1123 |
| Ser | Gly 325 | Pro | Thr | Phe | Leu | Ala 330 | Leu | Asn | Trp | Leu | Gly 335 | Tyr | Ala | Asn | Ser | |
| GCC | TTC | AAC | CCG | CTC | ATC | TAC | TGC | CGC | AGC | CCG | GAC | TTT | CGG | AGC | GCC | 1171 |
| Ala 340 | Phe | Asn | Pro | Leu | Ile 345 | Tyr | Cys | Arg | Ser | Pro 350 | Asp | Phe | Arg | Ser | Ala 355 | |
| TTC | CGC | CGC | CTG | CTG | TGT | CGC | TGC | CGG | CCG | GAG | GAG | CAC | CTC | GCC | GCT | 1219 |
| Phe | Arg | Arg | Leu 360 | Leu | Cys | Arg | Cys | Arg 365 | Pro | Glu | Glu | His | Leu 370 | Ala | Ala | |
| GCC | TCC | CCG | CCC | CGA | GCC | CCC | TCC | GGC | GCC | CCC | ACG | GCC | CTG | ACC | AGC | 1267 |
| Ala | Ser | Pro | Pro 375 | Arg | Ala | Pro | Ser | Gly 380 | Ala | Pro | Thr | Ala | Leu 385 | Thr | Ser | |
| CCC | GCT | GGC | CCC | ATG | CAG | CCC | CCA | GAG | CTC | GAC | GGG | GCT | TCC | TGC | GGA | 1315 |
| Pro | Ala | Gly 390 | Pro | Met | Gln | Pro | Pro 395 | Glu | Leu | Asp | Gly | Ala 400 | Ser | Cys | Gly | |
| CTT | TCT | TAGGCCTTGA | AGAAACAACT | CCATTGATCC | GGAACCTTTG | GAAAGCCTCT | | | | | | | | | | 1371 |
| Leu | Ser 405 | | | | | | | | | | | | | | | |

```
GGCCGGCCTC GGTTCAGAAT GAGCCCCGTG GAGTTTCCCA GCTGGAAAAC TCTGCCCTCC    1431
CCAGCCTGAC GACTGGGTCC TGGGAGGAGG CGCGGGGGCT GACTGGGGAG GGGAAATCCT    1491
TACCAAGTGG GTTTTCGCTC TCTTTCTGAG AGAAGTTTTC TACACCCCAG CCCTGAACTT    1551
CACCGCTGCC TCAGCAGCTC CCGCGTCTGG TTTCCCATGC CAGGTGCCC  GGGCAGGAGC    1611
TGGGCTGCGT TTAGCCCCGG GACCCGCACC TGTCCCACTC GGGTGCTGTG TGCGCAGGGG    1671
CAAGGCGGGC ACCTTCATTC TGTTCCTTCT GCCGCCCAGA CCCTGAGGAA CCCACCGGGG    1731
TGCTGGAGGC CCAGGCTGAG AAGAGGAAGG TGGGGAAGGT CACGGTTTGG GCTTCTGTCC    1791
CTGGCTTCCT CACTGTAGAC ACACCTACCT CACAGCATTT TCAGGACTTT ACTTTAGCCT    1851
TTGGGGTGGG GGTGGGGGGG CGCTCCTGGT TTCCTGGGAA GGTGAACCAT TAGAATGGGT    1911
CCCTTTTCCT TTTGAAATCA AATTAATAAA TGTTACTGAA TGCAGTTTAA AAAAAAAAA    1971
AAAAAAAAAA AAAAAAAAAA AAAAAAAA                                       2000
```

( 2 ) INFORMATION FOR SEQ ID NO:2:

( i ) SEQUENCE CHARACTERISTICS:
        ( A ) LENGTH: 405 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Ala | Pro | Trp | Pro 5 | Pro | Gly | Asn | Ser | Ser 10 | Leu | Thr | Pro | Trp | Pro Asp 15 |
| Ile | Pro | Thr | Leu 20 | Ala | Pro | Asn | Thr | Ala 25 | Asn | Ala | Ser | Gly | Leu 30 | Pro Gly |
| Val | Pro | Trp 35 | Ala | Val | Ala | Leu | Ala 40 | Gly | Ala | Leu | Leu | Ala 45 | Leu | Ala Val |
| Leu | Ala 50 | Thr | Val | Gly | Gly | Asn 55 | Leu | Leu | Val | Ile | Val 60 | Ala | Ile | Ala Arg |
| Thr 65 | Pro | Arg | Leu | Gln | Thr 70 | Met | Thr | Asn | Val | Phe 75 | Val | Thr | Ser | Leu Ala 80 |

```
Thr Ala Asp Leu Val Val Gly Leu Leu Val Val Pro Pro Gly Ala Thr
                85                  90                  95
Leu Ala Leu Thr Gly His Trp Pro Leu Gly Val Thr Gly Cys Glu Leu
               100                 105                 110
Trp Thr Ser Val Asp Val Leu Cys Val Thr Ala Ser Ile Glu Thr Leu
           115                 120                 125
Cys Ala Leu Ala Val Asp Arg Tyr Leu Ala Val Thr Asn Pro Leu Arg
    130                 135                 140
Tyr Gly Ala Leu Val Thr Lys Arg Arg Ala Leu Ala Ala Val Val Leu
145                 150                 155                 160
Val Trp Val Val Ser Ala Ala Val Ser Phe Ala Pro Ile Met Ser Lys
                165                 170                 175
Trp Trp Arg Ile Gly Ala Asp Ala Glu Ala Gln Arg Cys His Ser Asn
               180                 185                 190
Pro Arg Cys Cys Thr Phe Ala Ser Asn Met Pro Tyr Ala Leu Leu Ser
           195                 200                 205
Ser Ser Val Ser Phe Tyr Leu Pro Leu Leu Val Met Leu Phe Val Tyr
    210                 215                 220
Ala Arg Val Phe Val Val Ala Thr Arg Gln Leu Arg Leu Leu Arg Arg
225                 230                 235                 240
Glu Leu Gly Arg Phe Pro Pro Glu Glu Ser Pro Pro Ala Pro Ser Arg
                245                 250                 255
Ser Gly Ser Pro Gly Leu Ala Gly Pro Cys Ala Ser Pro Ala Gly Val
           260                 265                 270
Pro Ser Tyr Gly Arg Arg Pro Ala Arg Leu Leu Pro Leu Arg Glu His
    275                 280                 285
Arg Ala Leu Arg Thr Leu Gly Leu Ile Met Gly Thr Phe Thr Leu Cys
290                 295                 300
Trp Leu Pro Phe Phe Val Val Asn Val Val Arg Ala Leu Gly Gly Pro
305                 310                 315                 320
Ser Leu Val Ser Gly Pro Thr Phe Leu Ala Leu Asn Trp Leu Gly Tyr
           325                 330                 335
Ala Asn Ser Ala Phe Asn Pro Leu Ile Tyr Cys Arg Ser Pro Asp Phe
    340                 345                 350
Arg Ser Ala Phe Arg Arg Leu Leu Cys Arg Cys Arg Pro Glu Glu His
        355                 360                 365
Leu Ala Ala Ala Ser Pro Pro Arg Ala Pro Ser Gly Ala Pro Thr Ala
    370                 375                 380
Leu Thr Ser Pro Ala Gly Pro Met Gln Pro Pro Glu Leu Asp Gly Ala
385                 390                 395                 400
Ser Cys Gly Leu Ser
                405
```

( 2 ) INFORMATION FOR SEQ ID NO:3:

( i ) SEQUENCE CHARACTERISTICS:
        ( A ) LENGTH: 408 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Met Ala Pro Trp Pro His Glu Asn Ser Ser Leu Ala Pro Trp Pro Asp
1               5                   10                  15
```

| | | | | | | | | | | | | | | |
|---|---|---|---|---|---|---|---|---|---|---|---|---|---|---|
|Leu|Pro|Thr|Leu<br>20|Ala|Pro|Asn|Thr|Ala<br>25|Asn|Thr|Ser|Gly|Leu<br>30|Pro|Gly|
|Val|Pro|Trp<br>35|Glu|Ala|Ala|Leu|Ala<br>40|Gly|Ala|Leu|Leu<br>45|Ala|Leu|Ala|Val|
|Leu|Ala<br>50|Thr|Val|Gly|Gly|Asn<br>55|Leu|Leu|Val|Ile|Val<br>60|Ala|Ile|Ala|Trp|
|Thr<br>65|Pro|Arg|Leu|Gln|Thr<br>70|Met|Thr|Asn|Val|Phe<br>75|Val|Thr|Ser|Leu|Ala<br>80|
|Ala|Ala|Asp|Leu|Val<br>85|Met|Gly|Leu|Leu|Val<br>90|Val|Pro|Pro|Ala|Ala<br>95|Thr|
|Leu|Ala|Ile|Thr<br>100|Gly|His|Trp|Pro|Leu<br>105|Gly|Ala|Thr|Gly|Cys<br>110|Glu|Leu|
|Trp|Thr|Ser<br>115|Val|Asp|Val|Leu|Cys<br>120|Val|Thr|Ala|Ser|Ile<br>125|Glu|Thr|Leu|
|Cys|Ala<br>130|Ile|Ala|Val|Asp|Arg<br>135|Tyr|Leu|Ala|Val|Thr<br>140|Asn|Pro|Leu|Arg|
|Tyr<br>145|Gly|Ala|Leu|Val|Thr<br>150|Lys|Arg|Cys|Ala|Arg<br>155|Thr|Ala|Val|Val|Leu<br>160|
|Val|Trp|Val|Val|Ser<br>165|Ala|Ala|Val|Ser|Phe<br>170|Ala|Pro|Ile|Met|Ser<br>175|Gln|
|Trp|Trp|Arg|Val<br>180|Gly|Ala|Asp|Ala|Glu<br>185|Ala|Gln|Arg|Cys|His<br>190|Ser|Asn|
|Pro|Arg|Cys<br>195|Cys|Ala|Phe|Ala|Ser<br>200|Asn|Met|Pro|Tyr|Val<br>205|Leu|Leu|Ser|
|Ser|Ser<br>210|Val|Ser|Phe|Tyr|Leu<br>215|Pro|Leu|Leu|Val|Met<br>220|Leu|Phe|Val|Tyr|
|Ala<br>225|Arg|Val|Phe|Val|Val<br>230|Ala|Thr|Arg|Gln|Leu<br>235|Arg|Leu|Leu|Arg|Gly<br>240|
|Glu|Leu|Gly|Arg|Phe<br>245|Pro|Pro|Glu|Glu|Ser<br>250|Pro|Pro|Ala|Pro|Ser<br>255|Arg|
|Ser|Leu|Ala|Pro<br>260|Ala|Pro|Val|Gly|Thr<br>265|Cys|Ala|Pro|Pro|Glu<br>270|Gly|Val|
|Pro|Ala|Cys<br>275|Gly|Arg|Arg|Pro|Ala<br>280|Arg|Leu|Leu|Pro|Leu<br>285|Arg|Glu|His|
|Arg|Ala<br>290|Leu|Cys|Thr|Leu|Gly<br>295|Leu|Ile|Met|Gly|Thr<br>300|Phe|Thr|Leu|Cys|
|Trp<br>305|Leu|Pro|Phe|Phe|Leu<br>310|Ala|Asn|Val|Ile|Arg<br>315|Ala|Leu|Gly|Gly|Pro<br>320|
|Ser|Leu|Val|Pro|Gly<br>325|Pro|Ala|Phe|Leu|Ala<br>330|Leu|Asn|Trp|Leu|Gly<br>335|Tyr|
|Ala|Asn|Ser|Ala<br>340|Phe|Asn|Pro|Leu|Ile<br>345|Tyr|Cys|Arg|Ser|Pro<br>350|Asp|Phe|
|Arg|Ser|Ala<br>355|Phe|Arg|Arg|Leu|Leu<br>360|Cys|Arg|Cys|Gly|Arg<br>365|Arg|Leu|Pro|
|Pro|Glu<br>370|Pro|Cys|Ala|Ala|Ala<br>375|Arg|Pro|Ala|Leu|Phe<br>380|Pro|Ser|Gly|Val|
|Pro<br>385|Ala|Ala|Arg|Ser|Ser<br>390|Pro|Ala|Gln|Pro|Arg<br>395|Leu|Cys|Gln|Arg|Leu<br>400|
|Asp|Gly|Ala|Ser|Trp<br>405|Gly|Val|Ser| | | | | | | | |

( 2 ) INFORMATION FOR SEQ ID NO:4:

( i ) SEQUENCE CHARACTERISTICS:

( A ) LENGTH: 400 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

| Met | Ala | Pro | Trp | Pro | His | Lys | Asn | Gly | Ser | Leu | Ala | Phe | Trp | Ser | Asp |
| 1 | | | | 5 | | | | | 10 | | | | | 15 | |

| Ala | Pro | Thr | Leu | Asp | Pro | Ser | Ala | Ala | Asn | Thr | Ser | Gly | Leu | Pro | Gly |
| | | | 20 | | | | | 25 | | | | | 30 | | |

| Val | Pro | Trp | Ala | Ala | Ala | Leu | Ala | Gly | Ala | Leu | Leu | Ala | Leu | Ala | Thr |
| | | | 35 | | | | 40 | | | | | 45 | | | |

| Val | Gly | Gly | Asn | Leu | Leu | Val | Ile | Thr | Ala | Ile | Ala | Arg | Thr | Pro | Arg |
| | 50 | | | | | 55 | | | | | 60 | | | | |

| Leu | Gln | Thr | Ile | Thr | Asn | Val | Phe | Val | Thr | Ser | Leu | Ala | Thr | Ala | Asp |
| 65 | | | | | 70 | | | | | 75 | | | | | 80 |

| Leu | Val | Val | Gly | Leu | Leu | Val | Met | Pro | Gly | Ala | Thr | Leu | Ala | Ile |
| | | | | 85 | | | | | 90 | | | | | 95 |

| Thr | Gly | His | Trp | Pro | Leu | Gly | Ala | Thr | Gly | Cys | Glu | Leu | Trp | Thr | Ser |
| | | | 100 | | | | | 105 | | | | | 110 | | |

| Val | Asp | Val | Leu | Cys | Val | Thr | Ala | Ser | Ile | Glu | Thr | Leu | Cys | Ala | Leu |
| | | 115 | | | | | 120 | | | | | 125 | | | |

| Ala | Val | Asp | Arg | Tyr | Leu | Ala | Val | Thr | Asn | Pro | Leu | Arg | Tyr | Gly | Thr |
| | 130 | | | | | 135 | | | | | 140 | | | | |

| Leu | Val | Thr | Lys | Arg | Arg | Ala | Arg | Ala | Ala | Val | Val | Leu | Val | Trp | Ile |
| 145 | | | | | 150 | | | | | 155 | | | | | 160 |

| Val | Ser | Ala | Thr | Val | Ser | Phe | Ala | Pro | Ile | Met | Ser | Gln | Trp | Trp | Arg |
| | | | | 165 | | | | | 170 | | | | | 175 | |

| Val | Gly | Ala | Asp | Ala | Glu | Ala | Gln | Glu | Cys | His | Ser | Asn | Pro | Arg | Cys |
| | | | 180 | | | | | 185 | | | | | 190 | | |

| Cys | Ser | Phe | Ala | Ser | Asn | Met | Pro | Tyr | Ala | Leu | Leu | Ser | Ser | Ser | Val |
| | | 195 | | | | | 200 | | | | | 205 | | | |

| Ser | Phe | Tyr | Leu | Pro | Leu | Leu | Val | Met | Leu | Phe | Val | Tyr | Ala | Arg | Val |
| | 210 | | | | | 215 | | | | | 220 | | | | |

| Phe | Val | Val | Ala | Lys | Arg | Gln | Arg | Arg | Leu | Leu | Arg | Arg | Glu | Leu | Gly |
| 225 | | | | | 230 | | | | | 235 | | | | | 240 |

| Arg | Phe | Pro | Pro | Glu | Glu | Ser | Pro | Arg | Ser | Pro | Ser | Arg | Ser | Pro | Ser |
| | | | | 245 | | | | | 250 | | | | | 255 | |

| Pro | Ala | Thr | Val | Gly | Thr | Pro | Thr | Ala | Ser | Asp | Gly | Val | Pro | Ser | Cys |
| | | | 260 | | | | 265 | | | | | 270 | | | |

| Gly | Arg | Arg | Pro | Ala | Arg | Leu | Leu | Pro | Leu | Gly | Glu | His | Arg | Ala | Leu |
| | | 275 | | | | | 280 | | | | | 285 | | | |

| Arg | Thr | Leu | Gly | Leu | Ile | Met | Gly | Ile | Phe | Ser | Leu | Cys | Trp | Leu | Pro |
| | 290 | | | | | 295 | | | | | 300 | | | | |

| Phe | Phe | Leu | Ala | Asn | Val | Ile | Arg | Ala | Leu | Val | Gly | Pro | Ser | Leu | Val |
| 305 | | | | | 310 | | | | | 315 | | | | | 320 |

| Pro | Ser | Gly | Val | Phe | Ile | Ala | Leu | Asn | Trp | Leu | Gly | Tyr | Ala | Asn | Ser |
| | | | | 325 | | | | | 330 | | | | | 335 | |

| Ala | Phe | Asn | Pro | Leu | Ile | Tyr | Cys | Arg | Ser | Pro | Asp | Phe | Arg | Asp | Ala |
| | | | 340 | | | | 345 | | | | | 350 | | | |

| Phe | Arg | Arg | Leu | Leu | Cys | Ser | Tyr | Gly | Gly | Arg | Gly | Pro | Glu | Glu | Pro |
| | | 355 | | | | | 360 | | | | | 365 | | | |

| Arg | Val | Val | Thr | Phe | Pro | Ala | Ser | Pro | Val | Ala | Ser | Arg | Gln | Asn | Ser |
| | 370 | | | | | 375 | | | | | 380 | | | | |

```
Pro  Leu  Asn  Arg  Phe  Asp  Gly  Tyr  Glu  Gly  Glu  Arg  Pro  Phe  Pro  Thr
385                 390                 395                           400
```

(2) INFORMATION FOR SEQ ID NO:5:

(i) SEQUENCE CHARACTERISTICS:
(A) LENGTH: 400 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

```
Met  Ala  Pro  Trp  Pro  His  Arg  Asn  Gly  Ser  Leu  Ala  Leu  Trp  Ser  Asp
1                 5                      10                      15

Ala  Pro  Thr  Leu  Asp  Pro  Ser  Ala  Ala  Asn  Thr  Ser  Gly  Leu  Pro  Gly
                20                      25                      30

Val  Pro  Trp  Ala  Ala  Ala  Leu  Ala  Gly  Ala  Leu  Leu  Ala  Leu  Ala  Thr
           35                      40                      45

Val  Gly  Gly  Asn  Leu  Leu  Val  Ile  Ile  Ala  Ile  Ala  Arg  Thr  Pro  Arg
      50                      55                      60

Leu  Gln  Thr  Ile  Thr  Asn  Val  Phe  Val  Thr  Ser  Leu  Ala  Ala  Ala  Asp
65                      70                      75                      80

Leu  Val  Val  Gly  Leu  Leu  Val  Met  Pro  Pro  Gly  Ala  Thr  Leu  Ala  Leu
                 85                      90                      95

Thr  Gly  His  Trp  Pro  Leu  Gly  Glu  Thr  Gly  Cys  Glu  Leu  Trp  Thr  Ser
                100                     105                     110

Val  Asp  Val  Leu  Cys  Val  Thr  Ala  Ser  Ile  Glu  Thr  Leu  Cys  Ala  Leu
                115                     120                     125

Ala  Val  Asp  Arg  Tyr  Leu  Ala  Val  Thr  Asn  Pro  Leu  Arg  Tyr  Gly  Thr
           130                     135                     140

Leu  Val  Thr  Lys  Arg  Arg  Ala  Arg  Ala  Ala  Val  Leu  Val  Trp  Ile
145                     150                     155                     160

Val  Ser  Ala  Ala  Val  Ser  Phe  Ala  Pro  Ile  Met  Ser  Gln  Trp  Trp  Arg
                 165                     170                     175

Val  Gly  Ala  Asp  Ala  Glu  Ala  Gln  Glu  Cys  His  Ser  Asn  Pro  Arg  Cys
           180                     185                     190

Cys  Ser  Phe  Ala  Ser  Asn  Met  Pro  Tyr  Ala  Leu  Leu  Ser  Ser  Ser  Val
           195                     200                     205

Ser  Phe  Tyr  Leu  Pro  Leu  Leu  Val  Met  Leu  Phe  Val  Tyr  Ala  Arg  Val
      210                     215                     220

Phe  Val  Val  Ala  Lys  Arg  Gln  Arg  His  Leu  Leu  Arg  Arg  Glu  Leu  Gly
225                     230                     235                     240

Arg  Phe  Ser  Pro  Glu  Glu  Ser  Pro  Pro  Ser  Pro  Ser  Arg  Ser  Pro  Ser
                 245                     250                     255

Pro  Ala  Thr  Gly  Gly  Thr  Pro  Ala  Ala  Pro  Asp  Gly  Val  Pro  Pro  Cys
           260                     265                     270

Gly  Arg  Arg  Pro  Ala  Arg  Leu  Leu  Pro  Leu  Arg  Glu  His  Arg  Ala  Leu
           275                     280                     285

Arg  Thr  Leu  Gly  Leu  Ile  Met  Gly  Ile  Phe  Ser  Leu  Cys  Trp  Leu  Pro
      290                     295                     300

Phe  Phe  Leu  Ala  Asn  Val  Leu  Arg  Ala  Leu  Ala  Gly  Pro  Ser  Leu  Val
305                     310                     315                     320

Pro  Ser  Gly  Val  Phe  Ile  Ala  Leu  Asn  Trp  Leu  Gly  Tyr  Ala  Asn  Ser
                325                     330                     335

Ala  Phe  Asn  Pro  Val  Ile  Tyr  Cys  Arg  Ser  Pro  Asp  Phe  Arg  Asp  Ala
```

|  | | | | 340 | | | | | 345 | | | | | 350 | |
|---|---|---|---|---|---|---|---|---|---|---|---|---|---|---|---|

Phe Arg Arg Leu Leu Cys Ser Tyr Gly Gly Arg Gly Pro Glu Glu Pro
          355                     360                  365

Arg Ala Val Thr Phe Pro Ala Ser Pro Val Glu Ala Arg Gln Ser Pro
      370             375                 380

Pro Leu Asn Arg Phe Asp Gly Tyr Glu Gly Ala Arg Pro Phe Pro Thr
385                 390                 395                 400

( 2 ) INFORMATION FOR SEQ ID NO:6:

( i ) SEQUENCE CHARACTERISTICS:
        ( A ) LENGTH: 1218 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
ATGGCTCCGT  GGCCTCCTGG  GAACAGCTCT  CTGACCCCGT  GGCCAGATAT  CCCCACCCTG    60
GCACCCAATA  CTGCCAACGC  GAGTGGGCTG  CCAGGGGTGC  CCTGGGCGGT  GGCGCTGGCG   120
GGGGCGCTGT  TGGCGCTAGC  GGTGCTGGCC  ACCGTGGGAG  GCAACCTGCT  GGTAATCGTG   180
GCCATCGCCC  GGACGCCGAG  ACTCCAGACC  ATGACCAACG  TGTTCGTGAC  TTCGCTGGCC   240
ACAGCCGACC  TGGTGGTGGG  GCTCCTGGTC  GTGCCCCCGG  GGCCACGTT   GGCGCTGACC   300
GGCCACTGGC  CCCTGGGCGT  CACCGGTTGC  GAGCTGTGGA  CCTCAGTGGA  CGTGCTGTGT   360
GTGACCGCCA  GCATCGAAAC  CCTGTGCGCC  CTGGCGGTGG  ACCGCTACCT  GGCCGTGACC   420
AACCCGCTGC  GCTACGGCGC  GCTGGTCACC  AAACGCCGCG  CCCTAGCAGC  CGTGGTCCTG   480
GTGTGGGTGG  TGTCCGCCGC  GGTGTCGTTT  GCGCCCATCA  TGAGCAAATG  GTGGCGCATC   540
GGGGCCGATG  CCGAGGCGCA  GCGTTGCCAC  TCCAACCCGC  GCTGCTGCAC  CTTCGCCTCC   600
AACATGCCCT  ACGCGCTGCT  CTCCTCCTCG  GTCTCGTTCT  ATCTTCCGCT  CCTGGTGATG   660
CTCTTCGTCT  ACGCACGAGT  TTTCGTGGTG  CCACGCGCC   AGCTGCGCTT  GCTGCGCCGG   720
GAGCTGGGTC  GCTTCCCGCC  AGAGGAGTCT  CCGCCGGCTC  CTTCTCGCTC  CGGATCCCCT   780
GGCCTGGCGG  GGCCGTGCGC  CTCGCCCGCG  GGGGTGCCCT  CCTACGGCCG  GCGGCCGGCG   840
CGCCTTCTGC  CTCTGCGGGA  ACACCGCGCC  CTGCGCACCT  TGGGGCTCAT  CATGGGAACC   900
TTCACTCTCT  GCTGGTTGCC  TTTCTTTGTG  GTCAACGTGG  TGCGCGCCCT  CGGGGGCCCC   960
TCTCTGGTGT  CCGGCCCCAC  TTTCCTCGCC  CTTAACTGGC  TGGGCTATGC  CAACTCTGCC  1020
TTCAACCCGC  TCATCTACTG  CCGCAGCCCG  GACTTTCGGA  GCGCCTTCCG  CCGCCTGCTG  1080
TGTCGCTGCC  GGCCGGAGGA  GCACCTCGCC  GCTGCCTCCC  CGCCCCGAGC  CCCCTCCGGC  1140
GCCCCACGG   CCCTGACCAG  CCCCGCTGGC  CCCATGCAGC  CCCAGAGCT   CGACGGGGCT  1200
TCCTGCGGAC  TTTCTTAG                                                    1218
```

( 2 ) INFORMATION FOR SEQ ID NO:7:

( i ) SEQUENCE CHARACTERISTICS:
        ( A ) LENGTH: 1227 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
ATGGCTCCGT  GGCCTCACGA  GAACAGCTCT  CTTGCCCCAT  GGCCGGACCT  CCCCACCCTG    60
```

-continued

```
GCGCCCAATA CCGCCAACAC CAGTGGGCTG CCAGGGGTTC CGTGGGAGGC GGCCCTAGCC      120
GGGGCCCTGC TGGCGCTGGC GGTGCTGGCC ACCGTGGGAG GCAACCTGCT GGTCATCGTG      180
GCCATCGCCT GGACTCCGAG ACTCCAGACC ATGACCAACG TGTTCGTGAC TTCGCTGGCC      240
GCAGCCGACC TGGTGATGGG ACTCCTGGTG GTGCCGCCGG CGGCCACCTT GGCGCTGACT      300
GGCCACTGGC CGTTGGGCGC CACTGGCTGC GAGCTGTGGA CCTCGGTGGA CGTGCTGTGT      360
GTGACCGCCA GCATCGAAAC CCTGTGCGCC CTGGCCGTGG ACCGCTACCT GGCTGTGACC      420
AACCCGCTGC GTTACGGGGC ACTGGTCACC AAGCGCTGCG CCCGGACAGC TGTGGTCCTG      480
GTGTGGGTCG TGTCGGCCGC GGTGTCGTTT GCGCCCATCA TGAGCCAGTG GTGGCGCGTA      540
GGGGCCGACG CCGAGGCGCA GCGCTGCCAC TCCAACCCGC GCTGCTGTGC CTTCGCCTCC      600
AACATGCCCT ACGTGCTGCT GTCCTCCTCC GTCTCCTTCT ACCTTCCTCT TCTCGTGATG      660
CTCTTCGTCT ACGCGCGGGT TTTCGTGGTG GCTACGCGCC AGCTGCGCTT GCTGCGCGGG      720
GAGCTGGGCC GCTTTCCGCC CGAGGAGTCT CCGCCGGCGC CGTCGCGCTC TCTGGCCCCG      780
GCCCCGGTGG GGACGTGCGC TCCGCCCGAA GGGGTGCCCG CCTGCGGCCG GCGGCCCGCG      840
CGCCTCCTGC CTCTCCGGGA ACACCGGGCC CTGTGCACCT TGGGTCTCAT CATGGGCACC      900
TTCACTCTCT GCTGGTTGCC CTTCTTTCTG GCCAACGTGC TGCGCGCCCT GGGGGGCCCC      960
TCTCTAGTCC CGGGCCCGGC TTTCCTTGCC CTGAACTGGC TAGGTTATGC CAATTCTGCC     1020
TTCAACCCGC TCATCTACTG CCGCAGCCCG GACTTTCGCA GCGCCTTCCG CCGTCTTCTG     1080
TGCCGGTGCG GCCGTCGCCT GCCTCCGGAG CCCTGCGCCG CCGCCCGCCC GGCCCTCTTC     1140
CCCTCGGGCG TTCCTGCGGC CCGGAGCAGC CCAGCGCAGC CCAGGCTTTG CCAACGGCTC     1200
GACGGGGCTT CTTGGGGAGT TTCTTAG                                        1227
```

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA primer"

( x i ) SEQUENCE DESCRIPTION: SEQ ID NO:8:

```
GGTGGCGACG ACTCCTGGAG CCCG                                             24
```

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA primer"

( x i ) SEQUENCE DESCRIPTION: SEQ ID NO:9:

```
TTGCACCCAG ACCAACTGGT AATG                                             24
```